(12) United States Patent
Radlwimmer et al.

(10) Patent No.: US 9,241,993 B2
(45) Date of Patent: Jan. 26, 2016

(54) INHIBITORS OF BRANCHED-CHAIN-AMINOTRANSFERASE-1 (BCAT1) FOR THE TREATMENT OF BRAIN TUMORS

(75) Inventors: Bernhard Radlwimmer, Heidelberg (DE); Martje Toenjes, Heidelberg (DE); Sebastian Barbus, Heidelberg (DE); Peter Lichter, Gaiberg (DE)

(73) Assignee: Deutsches Krebsforschungszentrum, Heidelberg (DE)

( * ) Notice: Subject to any disclaimer, the term of this patent is extended or adjusted under 35 U.S.C. 154(b) by 0 days.

(21) Appl. No.: 13/982,098

(22) PCT Filed: Jan. 27, 2012

(86) PCT No.: PCT/EP2012/000378
§ 371 (c)(1),
(2), (4) Date: Jul. 26, 2013

(87) PCT Pub. No.: WO2012/100957
PCT Pub. Date: Aug. 2, 2012

(65) Prior Publication Data
US 2013/0310545 A1    Nov. 21, 2013

(30) Foreign Application Priority Data
Jan. 28, 2011 (EP) .................................... 11000720

(51) Int. Cl.
| | | |
|---|---|---|
| *A61K 48/00* | (2006.01) | |
| *A61K 39/395* | (2006.01) | |
| *A61K 31/00* | (2006.01) | |
| *A61K 31/7088* | (2006.01) | |
| *A61K 31/713* | (2006.01) | |
| *C12N 15/113* | (2010.01) | |
| *A61K 31/196* | (2006.01) | |

(52) U.S. Cl.
CPC ............ *A61K 39/39558* (2013.01); *A61K 31/00* (2013.01); *A61K 31/196* (2013.01); *A61K 31/7088* (2013.01); *A61K 31/713* (2013.01); *C12N 15/113* (2013.01); *C12N 15/1137* (2013.01); *C12Y 206/01042* (2013.01); *C12N 2310/11* (2013.01); *C12N 2310/14* (2013.01); *C12N 2310/531* (2013.01)

(58) Field of Classification Search
None
See application file for complete search history.

(56) References Cited

U.S. PATENT DOCUMENTS 6,809,119 B2 * 10/2004 Hu et al. ........................ 514/604

OTHER PUBLICATIONS

Chen et al. Amino Acids 2009, 37:143-152.*
deBont et al. (Neuro-Oncology 10, 648-660, 2008).*
Vecht et al. Seminars in Oncology, vol. 30, No. 6, Suppl 19 Dec. 2003: pp. 49-52.*
"The Screening and Functional Study of Amplified Genes Located at Chromosome 12p12-11 in Nasopharyngeal Carcinoma", Nov. 2009, (one-hundred and thirty-four (134) pages).
http://www.cqvip.com, Herald of Medicine, vol. 26, No. 2 Feb. 2007, pp. 111-115.
Translation of Chinese Office Action dated Mar. 12, 2014 (six (6) pages).

* cited by examiner

*Primary Examiner* — Kimberly Chong
(74) *Attorney, Agent, or Firm* — Crowell & Moring LLP

(57) ABSTRACT

Described is a compound capable of reducing or inhibiting (a) the biological activity of branched-chain-aminotranferase-1 (BCAT1) or (b) the expression of the gene encoding BCAT1 for use in a method of treating a neoplasia. A preferred compound is 1-(aminomethyl) cyclohexaneacetic acid (gabapentin).

9 Claims, 21 Drawing Sheets a a b

SEQUENCE LISTING

```
<160> NUMBER OF SEQ ID NOS: 39

<210> SEQ ID NO 1
<211> LENGTH: 25
<212> TYPE: DNA
<213> ORGANISM: artificial sequence
<220> FEATURE:
<223> OTHER INFORMATION: primer

<400> SEQUENCE: 1
caactatgga gaatggtcct aagct                                          25

<210> SEQ ID NO 2
```

```
<211> LENGTH: 23
<212> TYPE: DNA
<213> ORGANISM: artificial sequence
<220> FEATURE:
<223> OTHER INFORMATION: primer

<400> SEQUENCE: 2
tgtccagtcg ctctcttctc ttc                                            23

<210> SEQ ID NO 3
<211> LENGTH: 19
<212> TYPE: DNA
<213> ORGANISM: artificial sequence
<220> FEATURE:
<223> OTHER INFORMATION: primer

<400> SEQUENCE: 3
gctacgaccc ttgggatct                                                 19

<210> SEQ ID NO 4
<211> LENGTH: 18
<212> TYPE: DNA
<213> ORGANISM: artificial sequence
<220> FEATURE:
<223> OTHER INFORMATION: primer

<400> SEQUENCE: 4
gtgccactgc cgctctct                                                  18

<210> SEQ ID NO 5
<211> LENGTH: 20
<212> TYPE: DNA
<213> ORGANISM: artificial sequence
<220> FEATURE:
<223> OTHER INFORMATION: primer

<400> SEQUENCE: 5
tggttgtctg agcctccttt                                                20

<210> SEQ ID NO 6
<211> LENGTH: 20
<212> TYPE: DNA
<213> ORGANISM: artificial sequence
<220> FEATURE:
<223> OTHER INFORMATION: primer

<400> SEQUENCE: 6
aagtccccac cacctctttt                                                20

<210> SEQ ID NO 7
<211> LENGTH: 21
<212> TYPE: DNA
<213> ORGANISM: artificial sequence
<220> FEATURE:
<223> OTHER INFORMATION: primer

<400> SEQUENCE: 7
cccattcttg atccaatttc a                                              21

<210> SEQ ID NO 8
<211> LENGTH: 18
<212> TYPE: DNA
<213> ORGANISM: artificial sequence
<220> FEATURE:
<223> OTHER INFORMATION: primer

<400> SEQUENCE: 8
```

```
cgagctggac gagaccat                                                    18

<210> SEQ ID NO 9
<211> LENGTH: 20
<212> TYPE: DNA
<213> ORGANISM: artificial sequence
<220> FEATURE:
<223> OTHER INFORMATION: primer

<400> SEQUENCE: 9
gagccgaact caagtttcca                                                  20

<210> SEQ ID NO 10
<211> LENGTH: 20
<212> TYPE: DNA
<213> ORGANISM: artificial sequence
<220> FEATURE:
<223> OTHER INFORMATION: primer

<400> SEQUENCE: 10
gaccacgatc ctctacaagc                                                  20

<210> SEQ ID NO 11
<211> LENGTH: 21
<212> TYPE: DNA
<213> ORGANISM: artificial sequence
<220> FEATURE:
<223> OTHER INFORMATION: primer

<400> SEQUENCE: 11
tcccacacag tgaagctgat g                                                21

<210> SEQ ID NO 12
<211> LENGTH: 20
<212> TYPE: DNA
<213> ORGANISM: artificial sequence
<220> FEATURE:
<223> OTHER INFORMATION: primer

<400> SEQUENCE: 12
actgaattca cccccactga                                                  20

<210> SEQ ID NO 13
<211> LENGTH: 20
<212> TYPE: DNA
<213> ORGANISM: artificial sequence
<220> FEATURE:
<223> OTHER INFORMATION: primer

<400> SEQUENCE: 13
cctccatgat gctgcttaca                                                  20

<210> SEQ ID NO 14
<211> LENGTH: 20
<212> TYPE: DNA
<213> ORGANISM: artificial sequence
<220> FEATURE:
<223> OTHER INFORMATION: primer

<400> SEQUENCE: 14
gaaccacggc actgattttc                                                  20

<210> SEQ ID NO 15
<211> LENGTH: 20
<212> TYPE: DNA
```

```
<213> ORGANISM: artificial sequence
<220> FEATURE:
<223> OTHER INFORMATION: primer

<400> SEQUENCE: 15
ccccaccatg ttctgaatct                                                  20

<210> SEQ ID NO 16
<211> LENGTH: 26
<212> TYPE: DNA
<213> ORGANISM: artificial sequence
<220> FEATURE:
<223> OTHER INFORMATION: primer

<400> SEQUENCE: 16
aaataactta acaccccaat ctaaac                                           26

<210> SEQ ID NO 17
<211> LENGTH: 25
<212> TYPE: DNA
<213> ORGANISM: artificial sequence
<220> FEATURE:
<223> OTHER INFORMATION: primer

<400> SEQUENCE: 17 aagttttgt tgtggaagtt gtttt                                             25

<210> SEQ ID NO 18
<211> LENGTH: 27
<212> TYPE: DNA
<213> ORGANISM: artificial sequence
<220> FEATURE:
<223> OTHER INFORMATION: primer

<400> SEQUENCE: 18
cacctaacca acaatcatta aacacta                                          27

<210> SEQ ID NO 19
<211> LENGTH: 25
<212> TYPE: DNA
<213> ORGANISM: artificial sequence
<220> FEATURE:
<223> OTHER INFORMATION: primer

<400> SEQUENCE: 19
tttgtttgag ggtattggaa gtaat                                            25

<210> SEQ ID NO 20
<211> LENGTH: 25
<212> TYPE: DNA
<213> ORGANISM: artificial sequence
<220> FEATURE:
<223> OTHER INFORMATION: primer

<400> SEQUENCE: 20
taactcctac ccacctccct actat                                            25

<210> SEQ ID NO 21
<211> LENGTH: 25
<212> TYPE: DNA
<213> ORGANISM: artificial sequence
<220> FEATURE:
<223> OTHER INFORMATION: primer

<400> SEQUENCE: 21
atagtaggga ggtgggtagg agtta                                            25
```

```
<210> SEQ ID NO 22
<211> LENGTH: 25
<212> TYPE: DNA
<213> ORGANISM: artificial sequence
<220> FEATURE:
<223> OTHER INFORMATION: primer

<400> SEQUENCE: 22
aaacactaaa actactcccc caaac                                          25

<210> SEQ ID NO 23
<211> LENGTH: 22
<212> TYPE: DNA
<213> ORGANISM: artificial sequence
<220> FEATURE:
<223> OTHER INFORMATION: primer

<400> SEQUENCE: 23
gtttggggga gtagttttag tg                                             22

<210> SEQ ID NO 24
<211> LENGTH: 23
<212> TYPE: DNA
<213> ORGANISM: artificial sequence
<220> FEATURE:
<223> OTHER INFORMATION: primer

<400> SEQUENCE: 24
ctccctacca actatatttc tta                                            23

<210> SEQ ID NO 25
<211> LENGTH: 25
<212> TYPE: DNA
<213> ORGANISM: artificial sequence
<220> FEATURE:
<223> OTHER INFORMATION: primer

<400> SEQUENCE: 25
atttatgagg gtgttagatt tgggt                                          25

<210> SEQ ID NO 26
<211> LENGTH: 25
<212> TYPE: DNA
<213> ORGANISM: artificial sequence
<220> FEATURE:
<223> OTHER INFORMATION: primer

<400> SEQUENCE: 26
ttaaaaactc ctccccaaaa aatac                                          25

<210> SEQ ID NO 27
<211> LENGTH: 26
<212> TYPE: DNA
<213> ORGANISM: artificial sequence
<220> FEATURE:
<223> OTHER INFORMATION: primer

<400> SEQUENCE: 27
ttgtttaggt ttagtatttt tatggg                                         26

<210> SEQ ID NO 28
<211> LENGTH: 25
<212> TYPE: DNA
<213> ORGANISM: artificial sequence
<220> FEATURE:
```

```
<223> OTHER INFORMATION: primer

<400> SEQUENCE: 28
accatttata aaaaaatctc caaaa                                            25

<210> SEQ ID NO 29
<211> LENGTH: 28
<212> TYPE: DNA
<213> ORGANISM: artificial sequence
<220> FEATURE:
<223> OTHER INFORMATION: primer

<400> SEQUENCE: 29
aaattattat taagtaaatg taggtggg                                         28

<210> SEQ ID NO 30
<211> LENGTH: 20
<212> TYPE: DNA
<213> ORGANISM: artificial sequence
<220> FEATURE:
<223> OTHER INFORMATION: primer

<400> SEQUENCE: 30
gaggaggagg agaaagagca                                                  20

<210> SEQ ID NO 31
<211> LENGTH: 18
<212> TYPE: DNA
<213> ORGANISM: artificial sequence
<220> FEATURE:
<223> OTHER INFORMATION: primer

<400> SEQUENCE: 31
gacagagcct cgcctcct                                                    18

<210> SEQ ID NO 32
<211> LENGTH: 20
<212> TYPE: DNA
<213> ORGANISM: artificial sequence
<220> FEATURE:
<223> OTHER INFORMATION: primer

<400> SEQUENCE: 32
tccctagtcc tccgttctga                                                  20

<210> SEQ ID NO 33
<211> LENGTH: 20
<212> TYPE: DNA
<213> ORGANISM: artificial sequence
<220> FEATURE:
<223> OTHER INFORMATION: primer

<400> SEQUENCE: 33
attccaagga gcatttgtgc                                                  20

<210> SEQ ID NO 34
<211> LENGTH: 22
<212> TYPE: DNA
<213> ORGANISM: artificial sequence
<220> FEATURE:
<223> OTHER INFORMATION: primer

<400> SEQUENCE: 34
gagggtgact aaggaactct gg                                               22
```

```
<210> SEQ ID NO 35
<211> LENGTH: 20
<212> TYPE: DNA
<213> ORGANISM: artificial sequence
<220> FEATURE:
<223> OTHER INFORMATION: primer

<400> SEQUENCE: 35
attgccattc cgtcatcact                                              20

<210> SEQ ID NO 36
<211> LENGTH: 19
<212> TYPE: DNA
<213> ORGANISM: artificial sequence
<220> FEATURE:
<223> OTHER INFORMATION: primer

<400> SEQUENCE: 36
gctacgaccc ttgggatct                                               19

<210> SEQ ID NO 37
<211> LENGTH: 20
<212> TYPE: DNA
<213> ORGANISM: artificial sequence
<220> FEATURE:
<223> OTHER INFORMATION: primer

<400> SEQUENCE: 37
tcgattcacg cacacatttt                                              20

<210> SEQ ID NO 38
<211> LENGTH: 18
<212> TYPE: DNA
<213> ORGANISM: artificial sequence
<220> FEATURE:
<223> OTHER INFORMATION: primer

<400> SEQUENCE: 38
ccgagggctc atttgcat                                                18

<210> SEQ ID NO 39
<211> LENGTH: 18
<212> TYPE: DNA
<213> ORGANISM: artificial sequence
<220> FEATURE:
<223> OTHER INFORMATION: primer

<400> SEQUENCE: 39
cacccgagtt cccagctc                                                18
```

INHIBITORS OF BRANCHED-CHAIN-AMINOTRANSFERASE-1 (BCAT1) FOR THE TREATMENT OF BRAIN TUMORS The instant application contains a Sequence Listing which has been submitted via EFS-web and is hereby incorporated by reference in its entirety.

The present invention provides a compound capable of reducing or inhibiting (a) the biological activity of branched-chain-aminotransferase-1 (BCAT1) or (b) the expression of the gene encoding BCAT1 for use in a method of treating a brain tumor.

Malignant human glioblastomas account for the largest number of human malignant brain tumors. So far, the treatment of gliomas includes neurosurgical techniques (resection or stereotactic procedures), radiation therapy and chemotherapy. The current standard of care for, e.g., astrocytic tumors involves surgical tumor resection that can be followed by chemotherapy with the oral alkylating agent temozolamide (TMZ) and radiotherapy. However, glioblastomas are considered as being incurable as they fail to respond to ionising radiation, chemotherapy and surgical resection. In other words, with these therapies only a very limited prolongation of the lifespan of patients can be achieved. This means that despite these therapies, the average life span after the cancer diagnosis is merely 12 to 16 months.

Thus, the technical problem underlying the present invention is to provide means for the therapy of brain tumors, preferably glioblastomas or astrocytic brain tumors, which overcome the disadvantages of the current therapies and improve the survival of patients.

The solution of said technical problem is achieved by providing the embodiments characterized in the claims.

During the experiments resulting in the present invention it was found that known BACT1 inhibitors, like gabapentin, which have been used so far for example as anticonvulsant drugs, represent a novel treatment option for cancer therapy, i.e. an effective therapy for neoplasias in general and in particular for the treatment of brain tumors like astrocytic brain tumors. They potentially act by targeting a molecular pathway that is not targeted by any established chemotherapy.

(a) Schematic representation of BCAA catabolism. BCAAs branched-chain amino acids; BCKAs, branched-chain ketoacids. (b,c) RNA expression of BCAT1 (b) and BCAT2 (c) in 70 astrocytic gliomas (41 $IDH^{wt}$ and 29 $IDH^{mut}$) normalized to expression in normal brain (dashed line). Data are expressed as mean±s.d. (two-tailed Student's t-test). *, P<0.05; *** P, <0.001. (d) Western blot showing expression of BCAT: protein in astrocytic gliomas with IDH1 and IDH2 wildtype genes (lanes 1-5), different mutations in the IDH2 (lanes 6-7) or IDH1 (lanes 8-12) genes, and normal brain (lane 13). AII, diffuse astrocytoma WHO grade II; AAIII, anaplastic astrocytoma WHO grade III; sGBIV, secondary glioblastoma WHO grade IV; pGBIV, primary glioblastoma WHO grade IV; AOIII anaplastic oligodendroglioma WHO grade III. (e-h) Immunohistochemical stainings of BCAT1 in an $IDH^{wt}$ primary glioblastoma (e), a primary glioblastoma with IDH1-R1321H mutation (f), a diffuse astrocytoma with IDH1-R132C mutation (g), and an anaplastic oligodendroglioma with IDH2-R172K mutation (h). (i,j) Immunohistochemical staining of IDH1-R1321H in the same tumors as in panels b and c, respectively demonstrating the complementarity of BCAT1 and IDH1-R132H staining. Scale bars: 50 μm. (k) Two-by-two table showing the significant correlation of BCAT1 protein expression and mutation status of the IDH1 and IDH2 genes in 81 gliomas (p<0.0001; Fisher's Exact Test).

Figure 2:
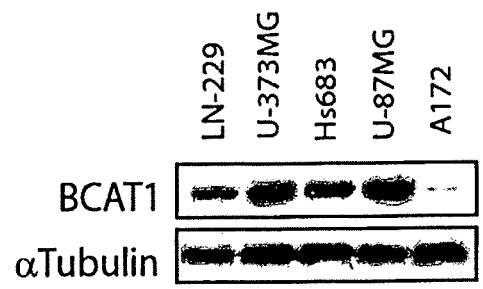
Figure 2:
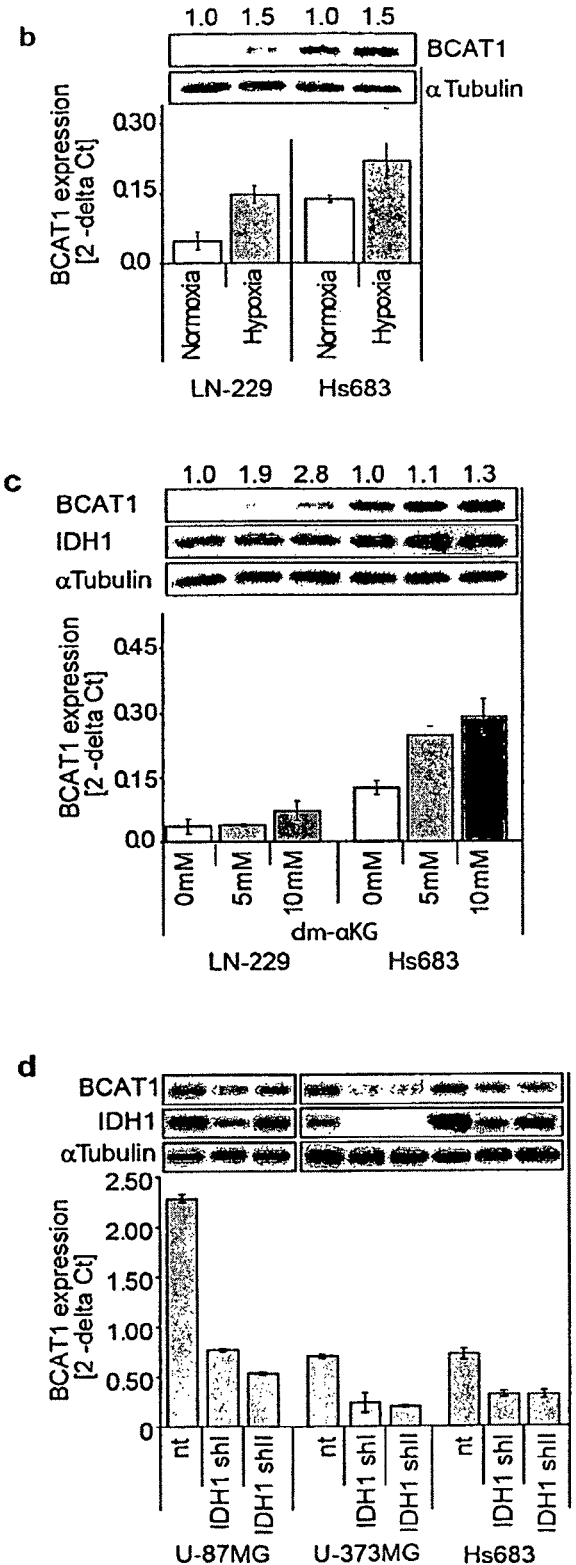

FIG. 2: BCAT1 shows substrate-dependent expression i glioblastoma cell lines.

(a) Western blot showing BCAT1 protein expression in $IDH^{wt}$ glioma cell lines. (b-d) Effects of hypoxia and alpha-KG on BCAT1 expression. RNA and protein expression are shown at the bottom and the top of each panel. The numbers above the Western blots indicate the fold ratios of expression relative to control cells. The mRNA expression values represent mean±s.d. of triplicate samples. (b) BCAT1 is upregulated under hypoxic (1% $O_2$) conditions. (c) BCAT1 expression is induced by supplementation of the culture media with cell-permeable dimethyl-alpha KG. (d) Knockdown by two different shRNAs of the alpha-KG-producing cytoplasmic IDH1 leads to downregulation of BCAT1 expression.

Figure 3:
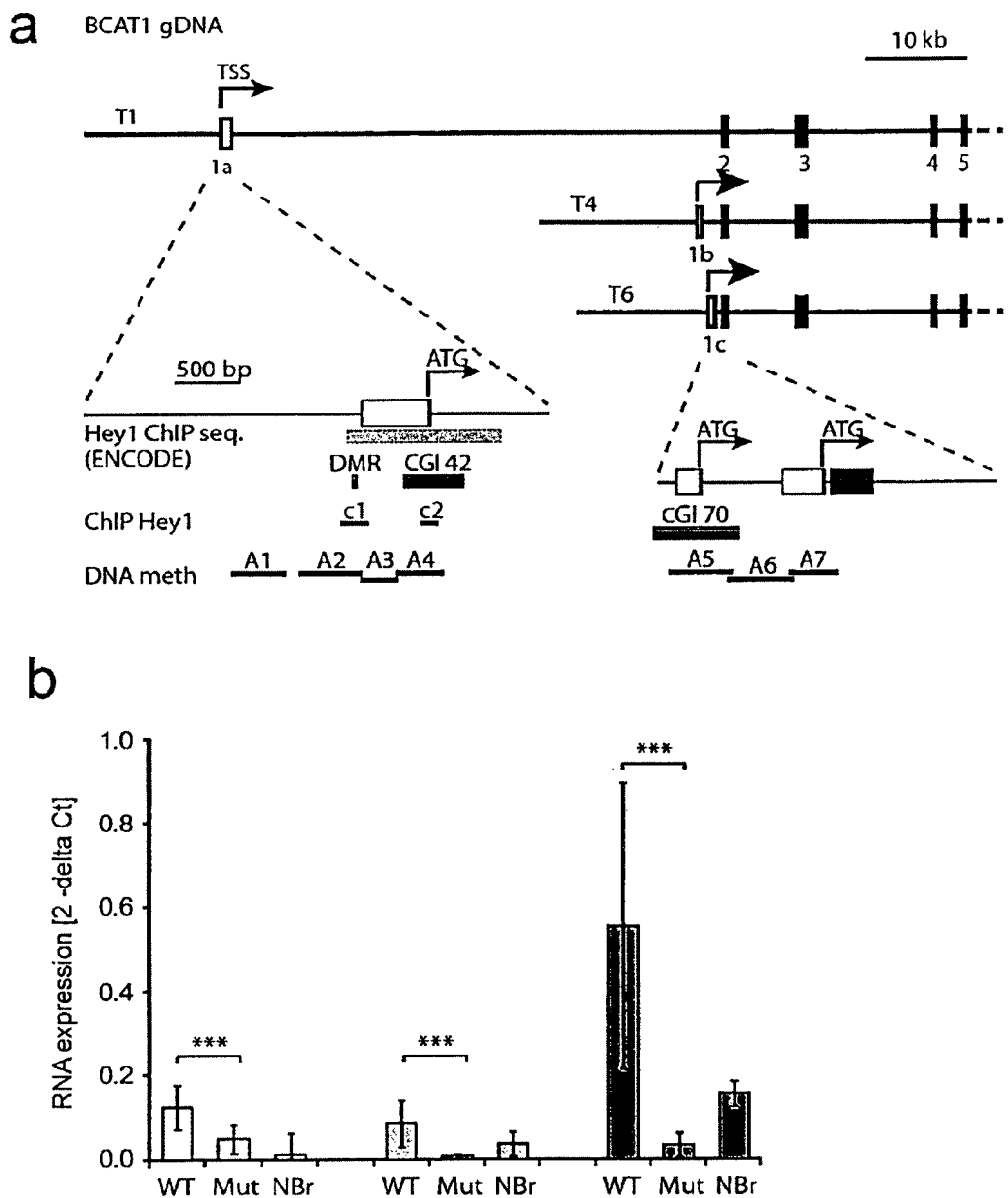
Figure 3:
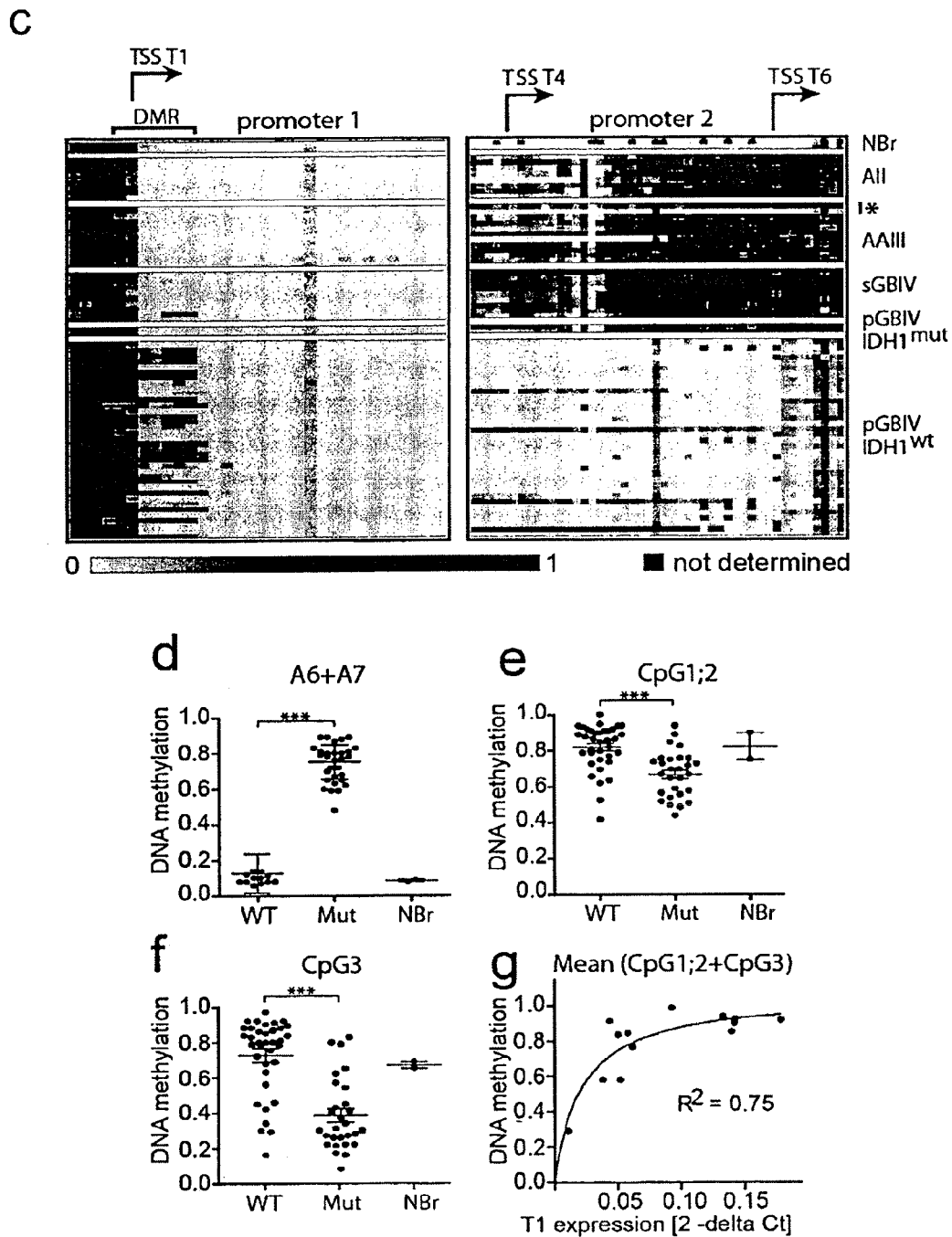
Figure 3:
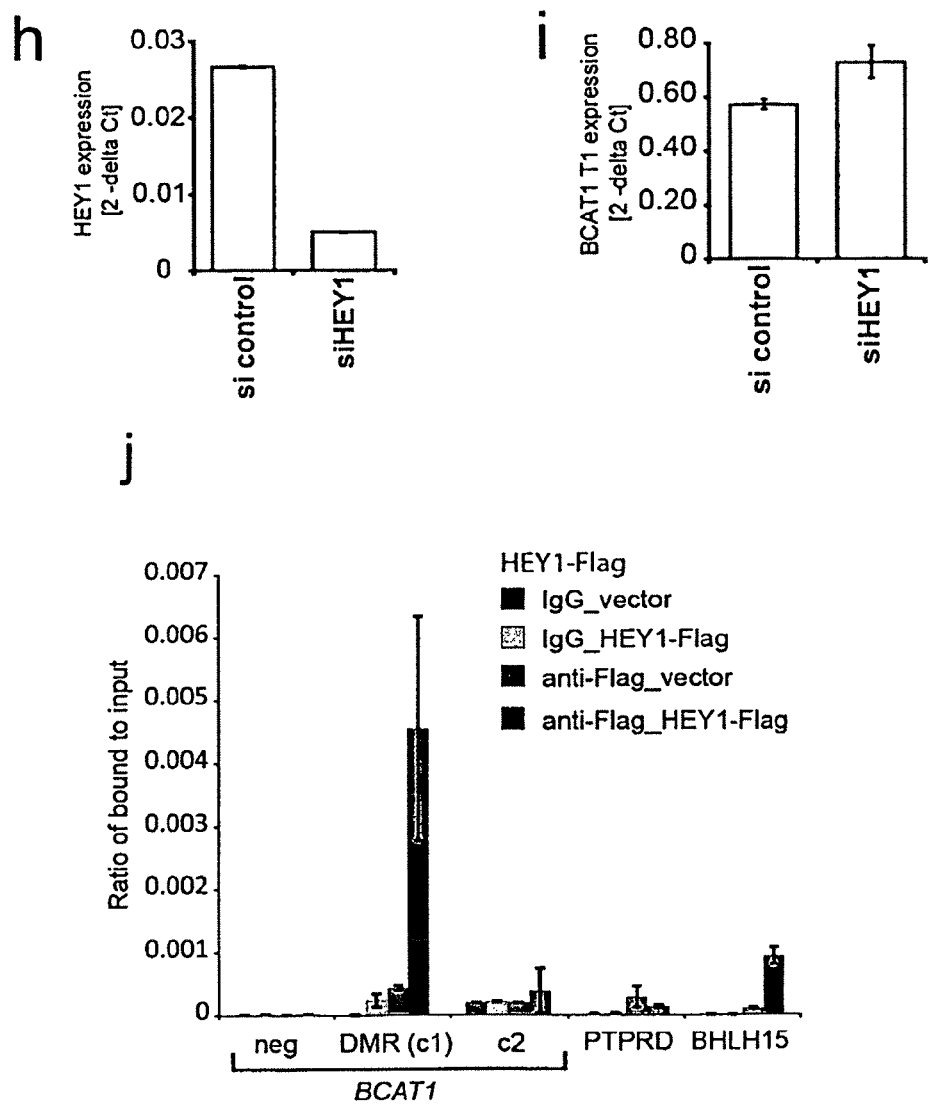
Figure 3:
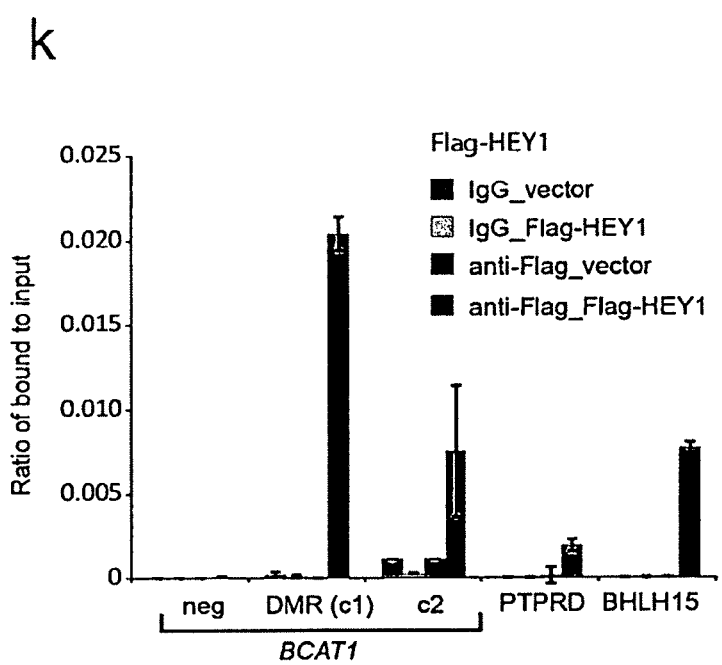

FIG. 3: Expression levels of the three BCAT1 transcripts are associated with differential methylation of two alternative promoters.

(a) Schematic drawing of exons 1 to 4 of BCAT1 showing the exon structure of the three transcripts T1, T4 and T6. The two alternative promoters 1 and 2 are shown in the enlarged sections on the lower left and lower right, respectively. (b) qRT-PCR quantification of RNA expression of transcripts T1, T4 and T6 in astrocytic gliomas and a pool of RNAs from normal brain tissues (n=23). Values represent mean±s.d. of triplicate samples. (c) DNA-methylation patterns detected in promoters 1 (left) and 2 (right) by massarray analysis of bisulfite-PCR amplicons A1 to A8 in normal brain and astrocytic gliomas WHO grade II-IV. *, IDHwt anaplastic astrocytoma. (d-f), Extent of DNA methylation in normal brain (Nbr), $IDH^{wt}$ and $IDH^{mut}$ tumors in (d) average of all CpGs in promoter 2 (two-tailed Student's t-test, P<0.0001) (e) CpG4, 5 (P=0.0003) and (f) CpG6 in promoter 1 (P<0.0001). (g) Correlation of CpG6 methylation grade and BCAT1 T1 expression (h,i) Knockdown of HEY1 in HEK293T cells (h) results in upregulation of BCAT1 expression (i). Values represent mean±s.d. (n=3). (j,k) ChIP assays showing preferred binding of HEY1 to the DMR (amplicon c1) as compared to control amplicons in promoter 1 (c2), about 5kb upstream of BCAT1, and unrelated positive (BHLH15) and negative (PT-PRD) controls. (j) Flag-HEY1 construct. (k) HEY1-Flag construct. qRT-PCR was performed in triplicate and ratios of bound to input are shown as mean±s.d.

Figure 4:
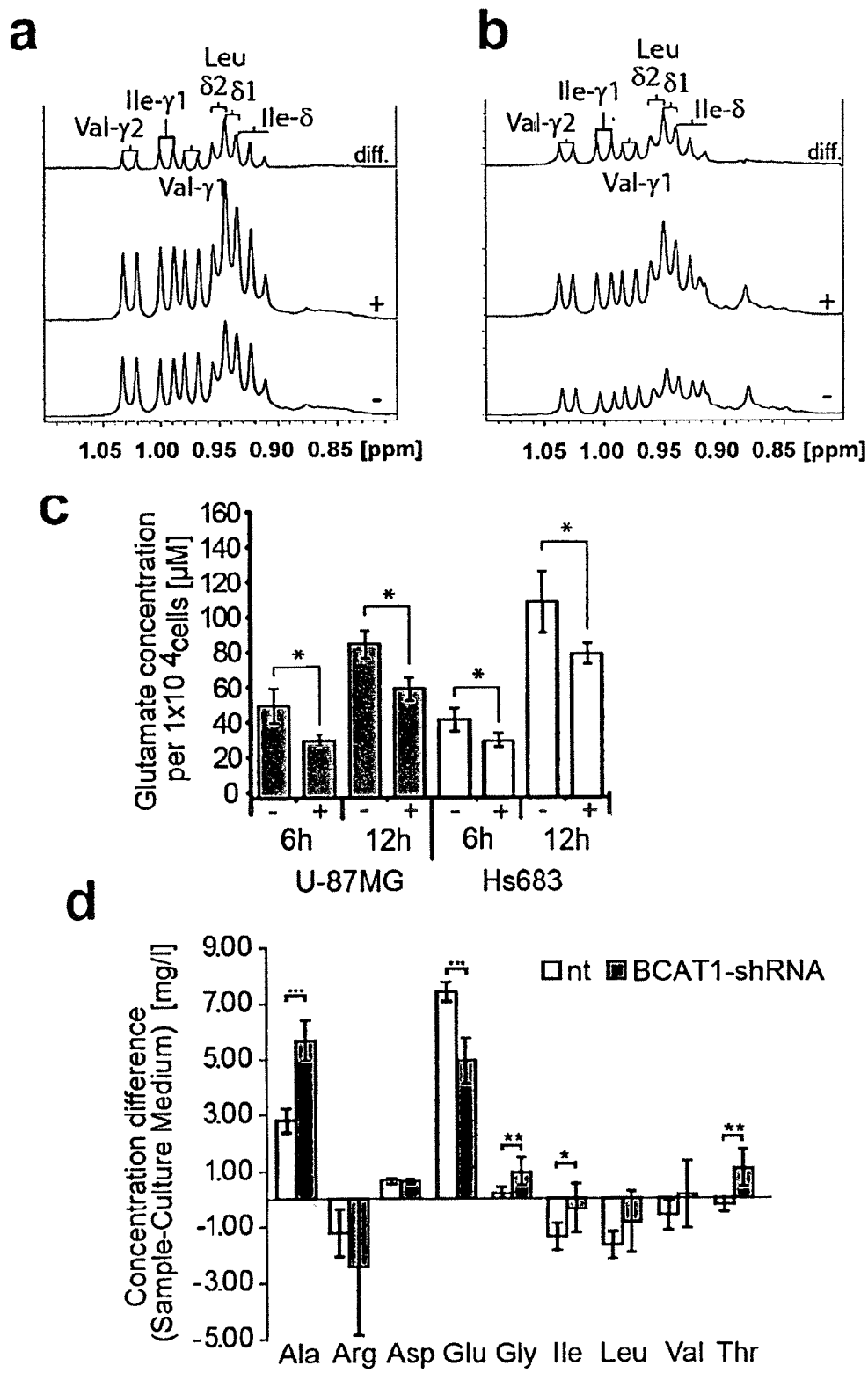
Figure 4:
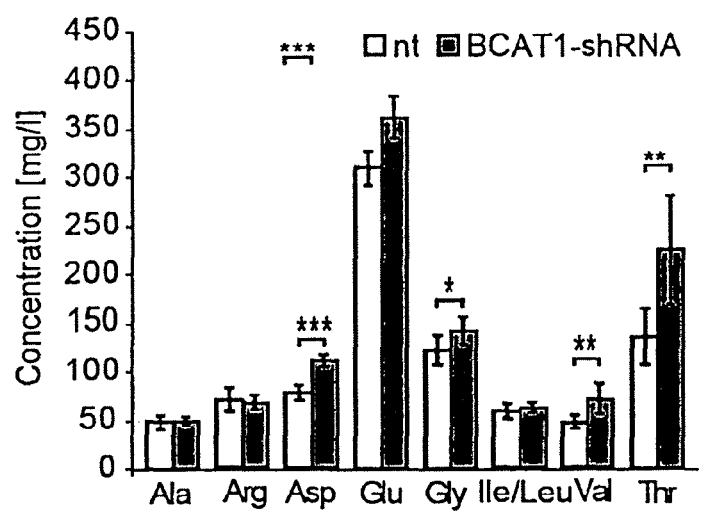
Figure 4:
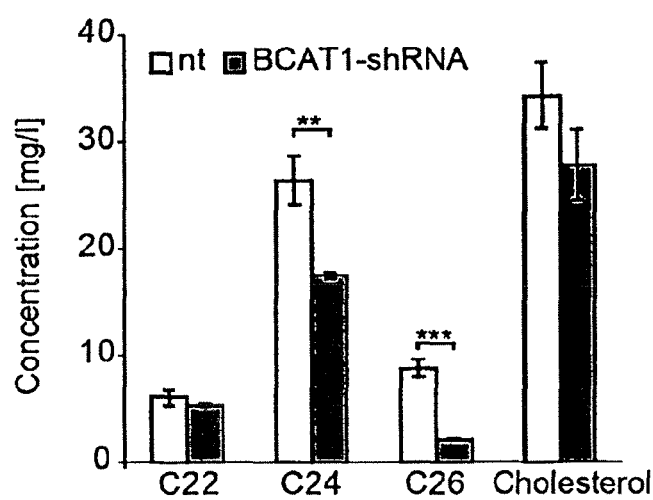
Figure 4:
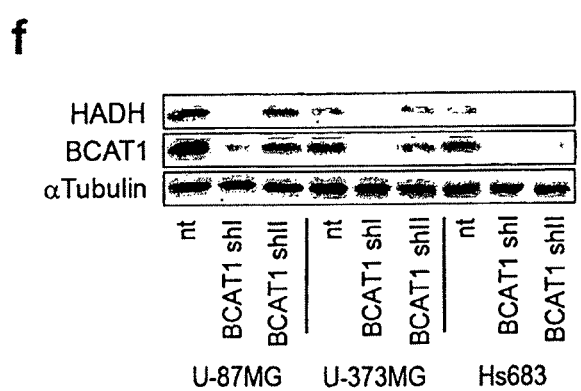

FIG. 4: BCAT1 suppression reduces glutamate release by glioma cells and affects concentrations of membrane fatty acids.

(a,b) NMR spectra of U-87MG (a) and U-373MG (b) cells after treatment with control (−) or 20 mM gabapentin (+) for 20 hours. Difference spectra are shown near the top of the panels. Upon inhibitor treatment levels of valine (Val), leucine (Leu) and isoleucine (Ile) increased by factors 1.09 1.38, 1.19, respectively, in U-87MG cells and by factors 1.83 2.18% and 2.32, respectively, in U-373MG cells. (c) Glutamate release by glioma cells at 6 and 12 hours after start of treatment with control (−) or with BCAT1 inhibition (+) by 20 mM gabapentin (n=3). (d) Tandem-MS analysis of amino acid concentrations in culture media of BCAT1 knockdown and control U-87MG cells 8 days after lentiviral transduction. Values are shown as difference to the media starting concentrations. Positive and negative values indicate amino acid release an uptake, respectively (n=6). (e) Intracellular amino acid concentrations of the same cells as in (d) (n=6). (f)

Western blot showing downregulation of HADH upon BCAT1 knockdown. (g) Relative depletion of cholesterol and very long chain fatty acids in BCAT1 knockdown vs. control U-87MG cells (n=3). Data are expressed as mean±s.d. *, P<0.05; , P<0.01; * P<0.001.

Figure 5:
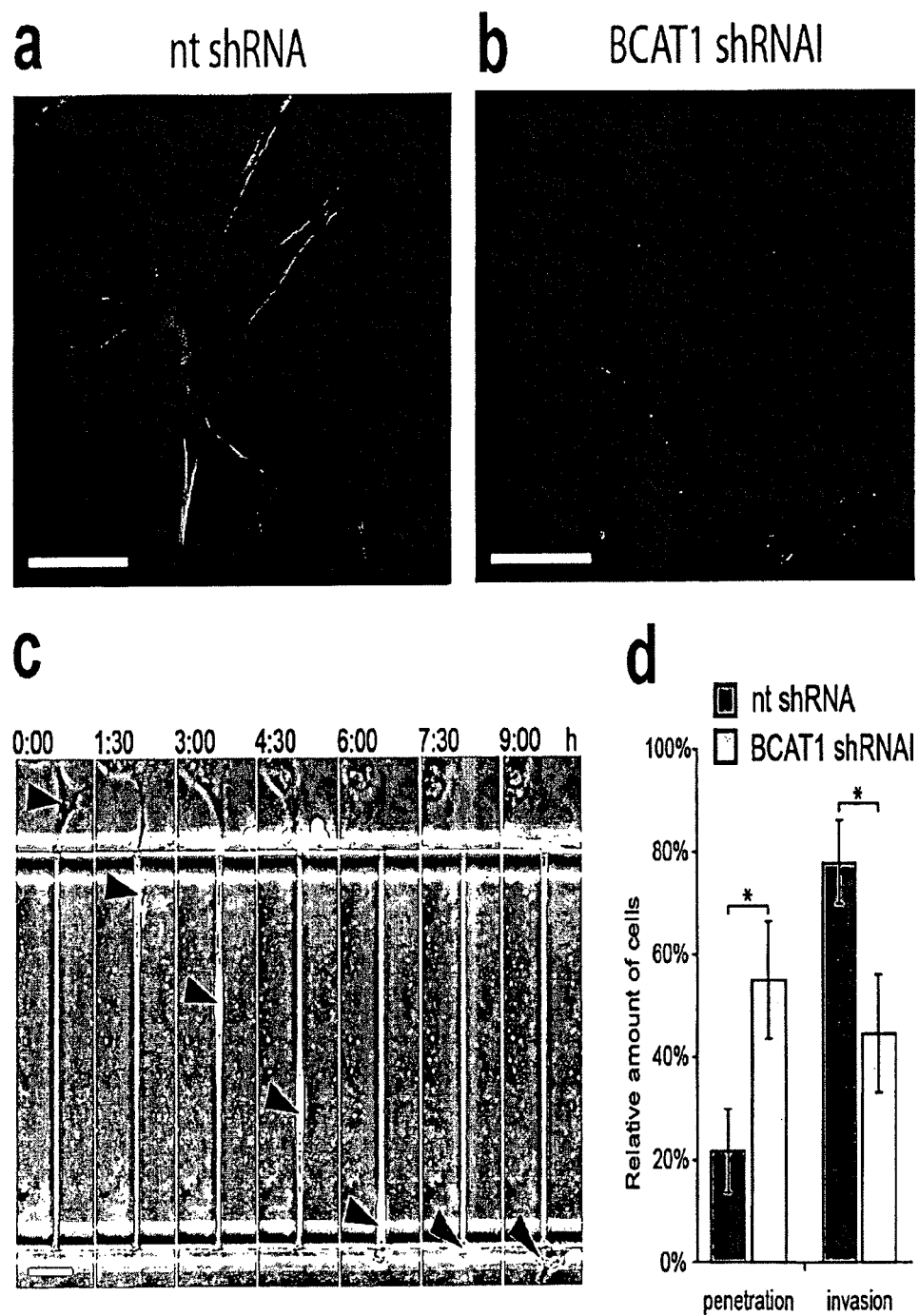

FIG. 5: BCAT1 knockdown limits glioblastoma cell invasion potential.

(a,b) Immuno-fluorescence labeling of alpha-tubulin in control (a) and BCAT1 knockdown (b) U-87MG cells. blue: DAPI; scale bar: 50 µm. (c) Sequential images showing the permeation of a U-87MG cell through a 5×11×300 pm microchannel over a period of 9 hours; scale bar: 50 µm. (d) BCAT1 knockdown significantly inhibits the invasion potential of U-87MG cells compared to nontarget shRNA transduced cells. Results indicate the mean±s.d. of three independent experiments. P=0.0146.

Figure 6:
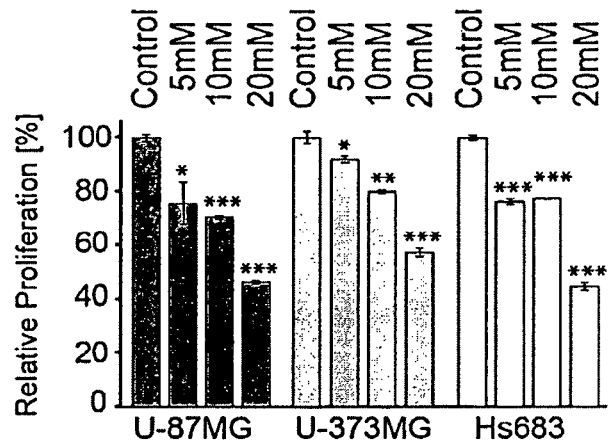
Figure 6:
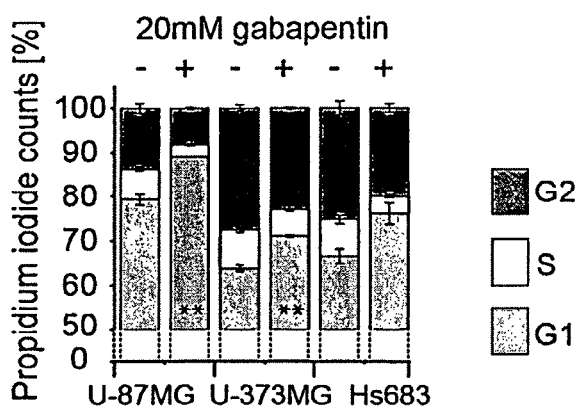
Figure 6:
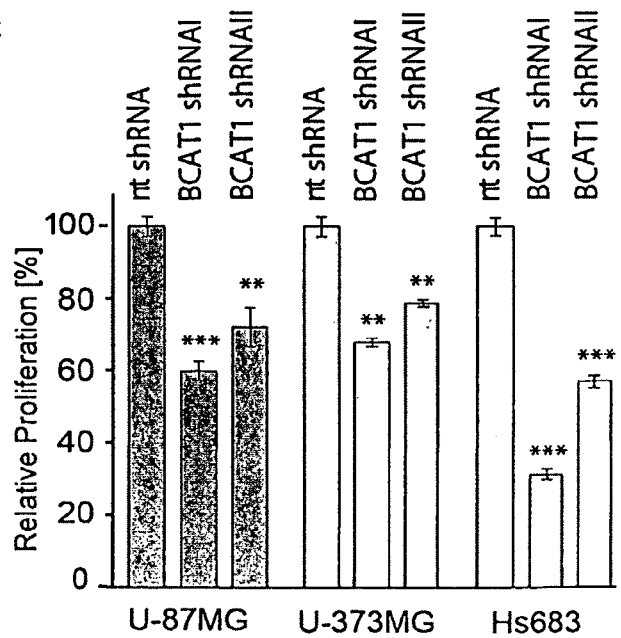
Figure 6:
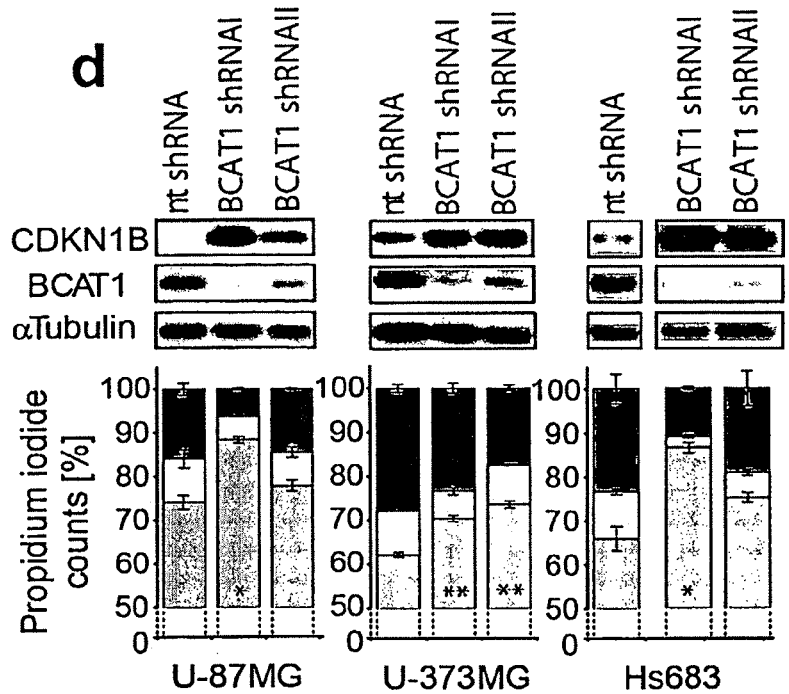
Figure 6:
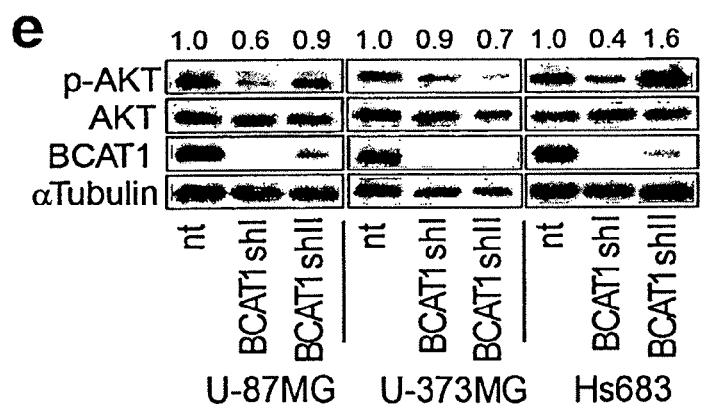
Figure 6:
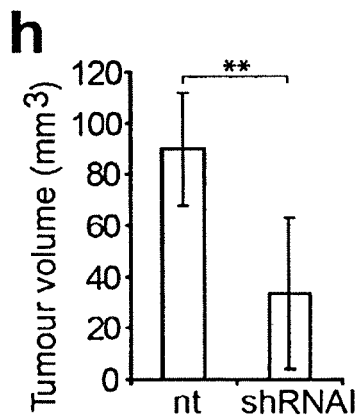
Figure 6:
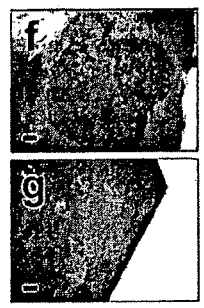

FIG. 6: BCAT1 is essential for glioblastoma progression.

(a-d) Cell proliferation and cell cycle analyses of glioma cells upon BCAT1 suppression. Proliferation of cells was examined using the Click-iT® EdU cell proliferation assay Cell cycle analysis was performed after DNA staining with propidium iodide. The DNA distribution is shown for living cells. Values in graphs represent mean ± s.d. for n=3. nt, nontarget shRNA. *, P<0.05; , P<0.01; * P<0.001; compared to respective controls. (a) Treatment with the BCAT1 inhibitor gabapentin for 20 hours suppressed proliferation of glioma cell lines in a concentration-dependent manner relative to control cells treated with solvent only. (b) Cell cycle analysis of gabapentin-treated glioma cells showed an accumulation of cells in G1-phase. (c) Knockdown of BCAT1 caused a significant reduction of cell proliferation relative to samples treated with nontarget shRNA (nt) in all three glioma cell lines and (d) resulted in the accumulation of the G1-arrest marker CDKN1B/p27$^{KIP1}$. Cell cycle analysis showed significant increases of the proportions of cells in G1 phase (e) BCAT1 knockdown results in decreased phosphorylation of AKT. (f-g) Cross-sections of tumors induced by intracranial injection of U-87MG glioblastoma cells into CD-1 nude mice. Hematoxylin-eosin staining is shown for mice injected with (f) control nontarget-shRNA or (g) BCAT1-shRNA. (h) Quantification of tumor volumes (n=5 mice for each group, P=0.0091).

Figure 7:
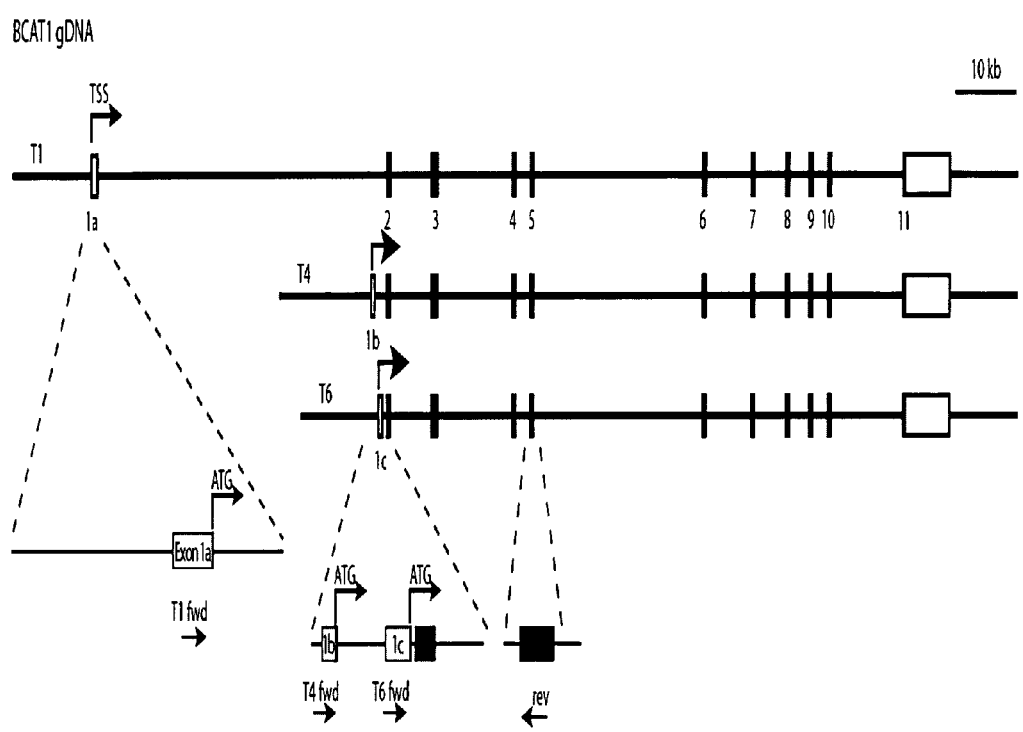
Figure 7:
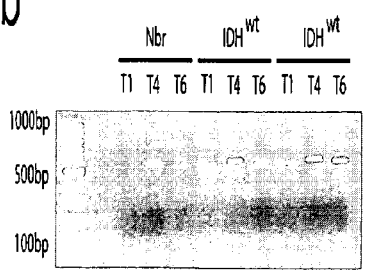

FIG. 7: BCAT1 transcripts.

(a) Gene structure of BCAT1 showing 11 exons and the three transcripts T1 (ENST00000261192), T4 (ENST00000539282) and T6 (ENST00000538118) which originate in two different promoters The regions around the transcription start sitzes (TSS) an exon 5 are enlarged to show primer locations. (b) Agarose gel image of PCR products amplified from an IDH$^{wt}$ glioblastoma (left) and a pool of normal brain RNAs from 23 individuals (right) using the reverse primer and the transcript-specific exon 1 primers. Band sizes match the expected sizes of the respective spliced mRNAs.

Figure 8:
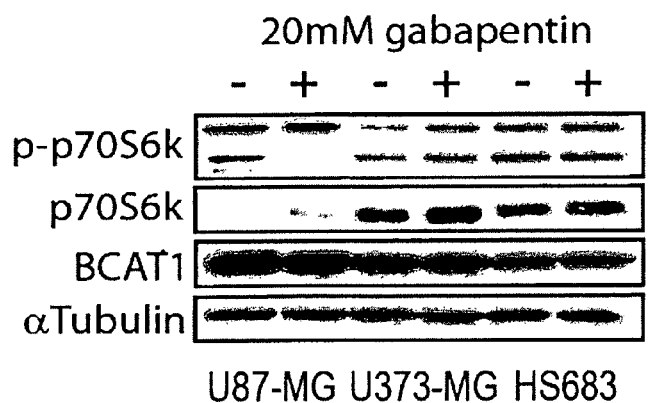
Figure 8:
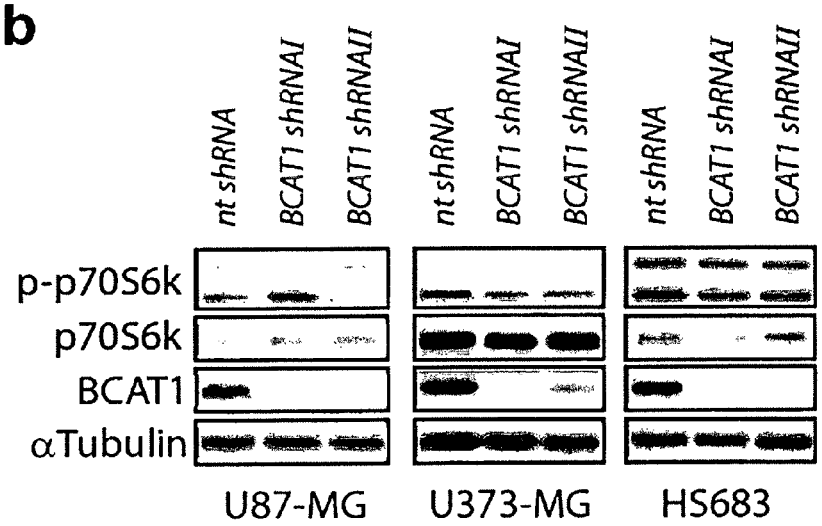

FIG. 8: Western blot analysis

Western Blot analysis of total and phosphorylated protein of the mTOR target RPS6K upon (a) gabapentin treatment and (b) BCAT1 knockdown in the cell lines U-87MG, U-373MG and Hs683.

Figure 9:
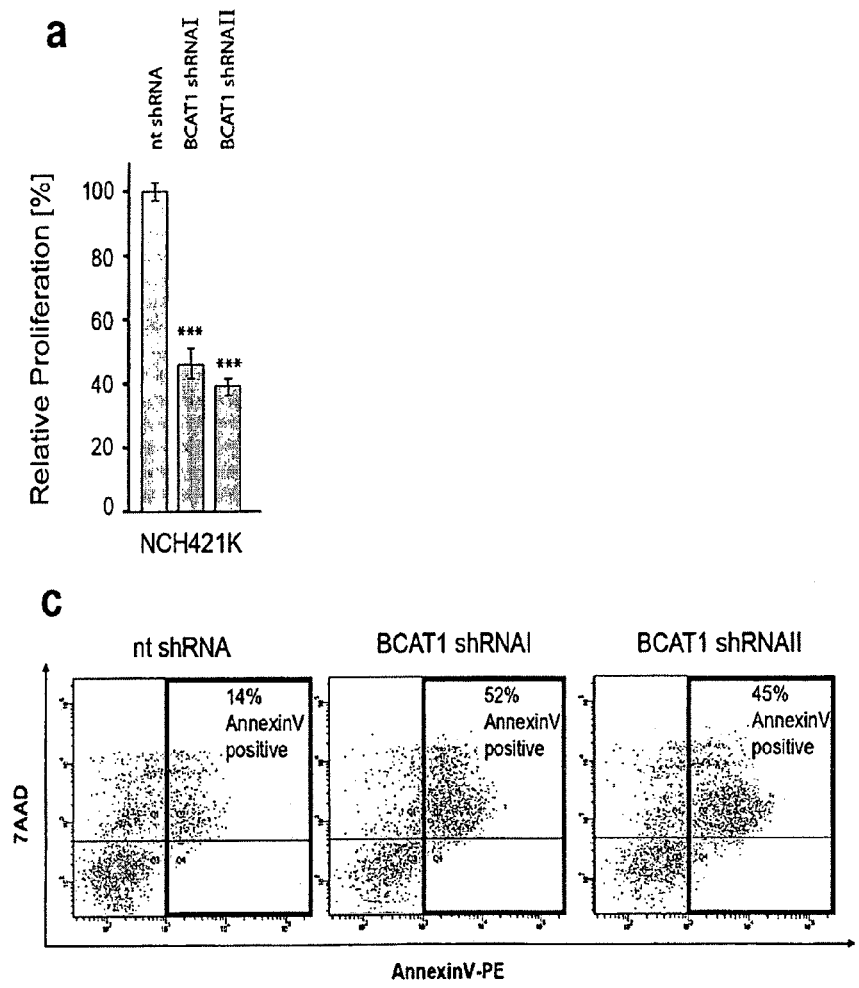
Figure 9:
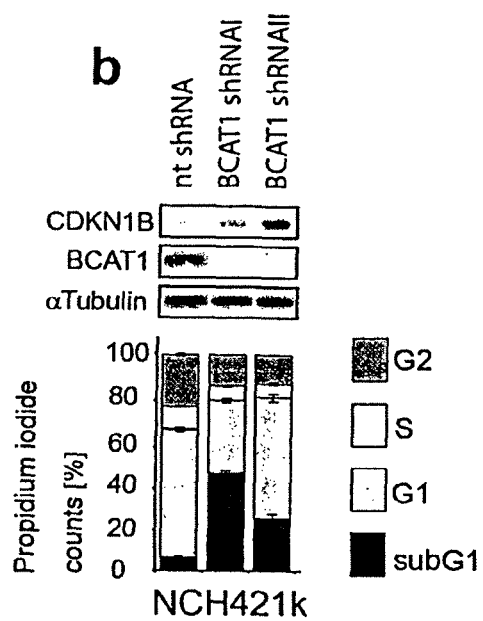

FIG. 9: BCAT1 knockdown

BCAT1 knockdown causes apoptosis in a glioblastoma spheroid primary culture. (a) Reduction of proliferation induced by lentiviral transduction of two shRNA constructs (n=3, *** P<0.0001). (b) Cell cycle analysis showing strong increase of the subGl fraction following BCAT1 knockdown (n=3). The Western blot at the top shows the increased presence of the G1-arrest marker CDKN1B in the knockdown cells. (c) AnnexinV/7AAD assay confirming apoptotic death of spheroid cells with BCAT1 knockdown.

Figure 10:
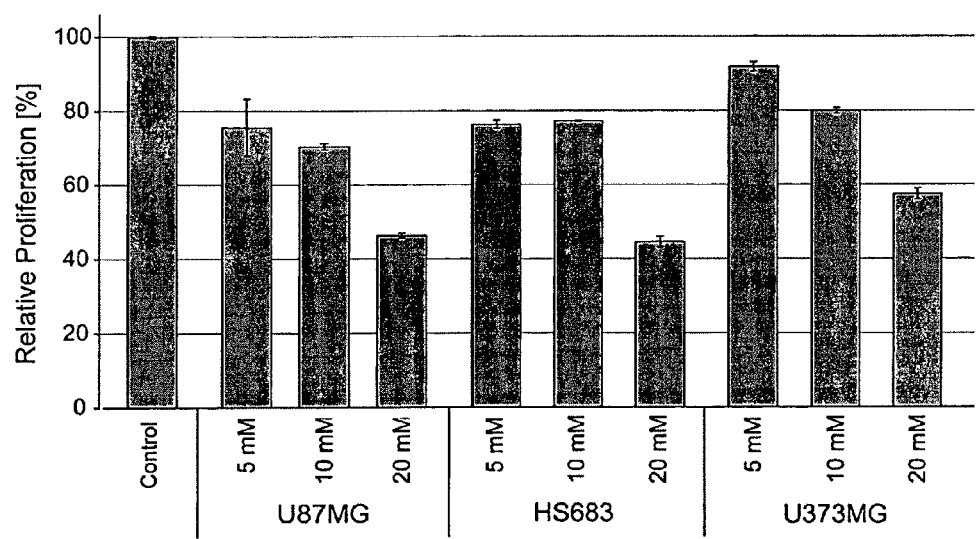

FIG. 10: Click-iT EdU assay after 5 mM Gabapentin treatment for 23 h

See Example 2 for experimental details.

Figure 11:
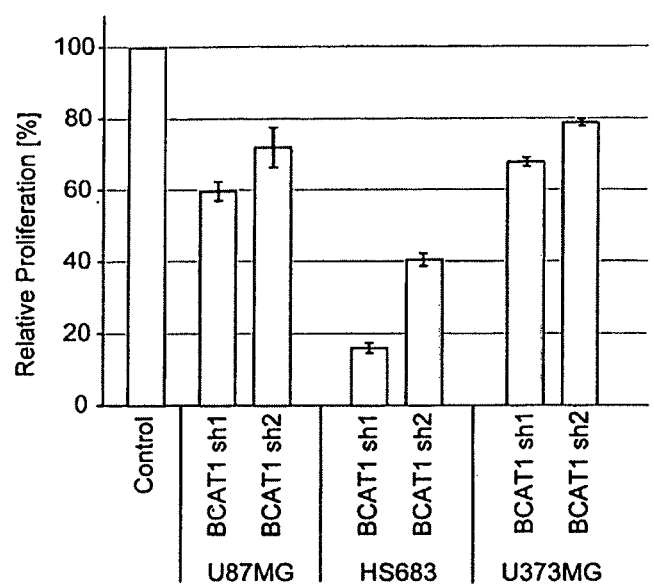

FIG. 11: Click-iT EdU assay after shRNA-mediated knock down

See Example 3 for experimental details

Thus, the present invention relates to a compound capable of reducing or inhibiting (a) the biological activity of branched-chain-aminotransferase-1 (BCAT1) or (b) the expression of the gene encoding BCAT1 for use in a method of treating a neoplasia.

"Neoplasm" is an abnormal mass of tissue as a result of neoplasia. "Neoplasia" is the abnormal proliferation of cells. The growth of the cells exceeds and is uncoordinated with respect to the normal tissues around it. The growth persists in the same excessive manner, even after cessation of the stimuli. It usually causes a lump or tumor. Neoplasms may be benign, pre-malignant (carcinoma-in-situ) or malignant (cancer). The neoplasms to be treated according to the present invention are those which (over)express BCAT1. Thus, the determination of BCAT1 in a neoplasm is an indication to start with a BCAT inhibiting therapy. Neoplasms to be treated are brain tumors, particularly an astrocytic brain tumor, glioma or glioblastoma, in particular those expressing IDH1 wildtype.

Figure 1:
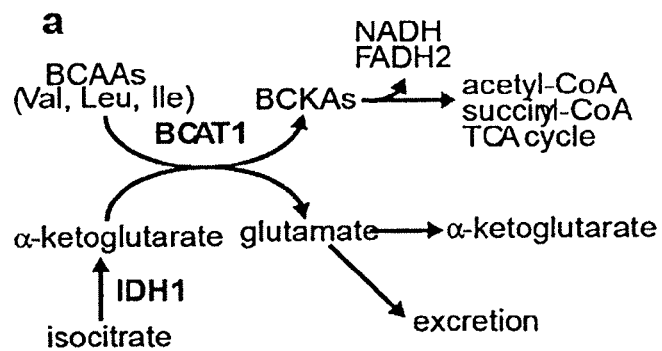
FIG. 1: $IDH^{wt}$ astrocytic gliomas are characterized by high BCAT1 expression.
Figure 1:
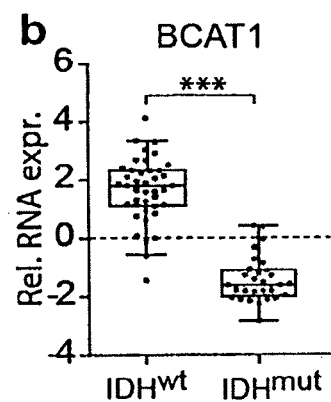
Figure 1:
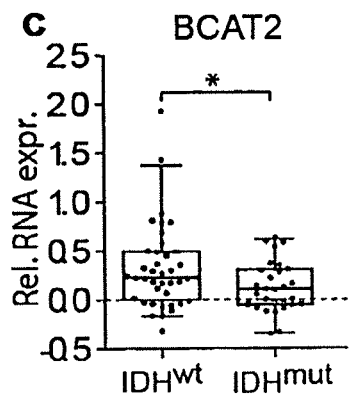
Figure 1:
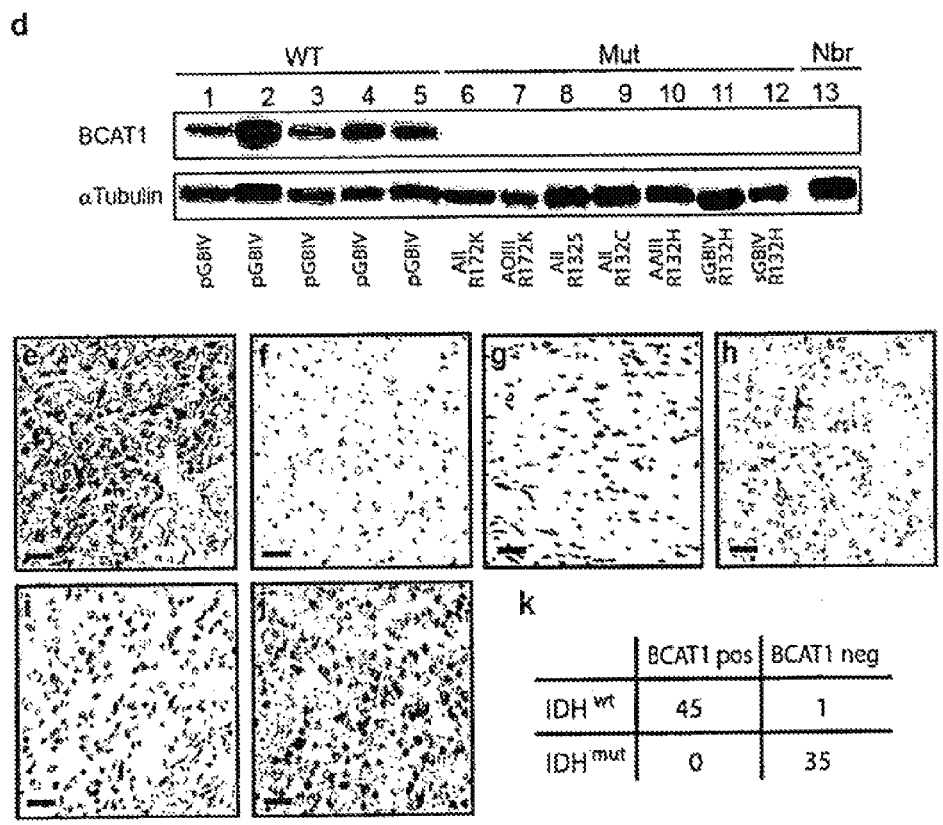

The branched-chain amino acids (BCAAs) valine, leucine and isoleucine are essential amino acids that escape liver catabolism and are available in the general circulation. BCAA metabolism provides an important transport system to move nitrogen throughout the body for the synthesis of nonessential amino acids, including the neurotransmitter glutamate in the central nervous system. Deregulation of the BCAA catabolic pathways frequently results in neural dysfunction. The first step of BCAA catabolism involves the transfer of the alpha-amino group to alpha-ketoglutarate (alpha-KG) by the cytosolic branched-chain amino acid transaminase 1 (BCAT1) or the mitochondrial BCAT2 isoenzymes with glutamate and the respective branched chain ketoacid (BCKA) as products (Ichihara et al., J. Biochem. 59, pp.160 169, (1966); Taylor et al., J. Biol. Chem. 241, pp. 4396-4405 (1966)). Expression of BCAT2 is ubiquitous, whereas expression of BCAT1 is restricted to a small number of tissues including brain, where BCAAs are a major source of nitrogen for the synthesis of the neurotransmitter glutamate. Following transamination, BCKAs are catabolized further to acetyl-CoA and succinyl-CoA, which enter the tricarboxylic acid (TCA) cycle (FIG. 1a). NADH and FADH2, which are generated as a by-product of BCKA catabolism, are used to transfer reducing equivalents to complex III of the respiratory chain for ATP production.

Mutations in IDH1 (isocitrat dehydrogenase 1), originally detected in a fraction of glioblastomas are present in the great majority of World Health Organization (WHO) grade II and III gliomas and secondary glioblastomas, but are rare in primary glioblastomas (Balss et al., Acta Neuropath. 116, pp. 597-602 (2008)). Mutations in IDH2 also have been detected, albeit at a lower frequency of 5-10% (Balss, Balss et al., Acta Neuropath. 116, pp. 597-602 (2008); Yan et al., N. Eng. J. Med. 360, pp. 765-773 (2009)). IDH mutations play a central role in glioma pathogenesis (Parsons et al, Science 321, pp. 1807-1812 (2008)) and have been shown to constitute a key classifier distinguishing two major glioma subgroups that were identified initially based on RNA expression and DNA methylation patterns. It has been revealed that brain tumors showing an IDH1 mutation (IDH$^{mut}$) have a better prognosis than those where IDH1 is not mutated (IDH$^{wt}$) (Hartmann et al., Acta Neuropathol. 120, pp. 707-718 (2010)).

The inventors found out that one difference between IDH$^{mut}$ (having IDH1-R132H mutation) and IDH$^{wt}$ brain tumors is that BCAT1 overexpression is a highly specific feature of IDH$^{wt}$ glioblastomas, the most common and most aggressive adult brain tumor. The observed specific methylation of the BCAT1 promoter 2 in IDH$^{mut}$ tumors, but not in IDH$^{wt}$ tumors and normal brain strongly show that low BCAT1 expression in IDH$^{mut}$ tumors is a consequence of IDH1 mutation-associated DNA methylation, which is thought to be mediated through inhibition of histone demethylases and the TET family of 5-methylcytosine hydroxylases by the product of mutant IDH1 and IDH2 enzymes, the oncometabolite 2-hydroxyglutarate. Interestingly, regulation of BCAT1 mRNA expression originating from promoter 1 appears to be achieved by an IDH-independent epigenetic mechanism, through methylation of a bindung site for the HEY1 transcriptional repressor in IDH$^{wt}$ but not IDH$^{mut}$ tumors. These diametrically opposed patterns of DNA methylation in the two promoters make clear that BCAT1 suppression does not occur as a mere byproduct of IDH1 mutation through "passenger" methylation, but rather that the differential regulation of cell metabolism in IDH$^{wt}$ and IDH$^{mut}$ tumors requires tight control of BCAT1 expression in each group.

Similar to the commonly used diagnostic IDH1-R132H staining BCAT1 staining may help to distinguish IDH$^{wt}$ from IDH$^{mut}$ gliomas; however, BCAT1 staining offers the added advantage of also distinguishing IDH$^{wt}$ primary glioblastoma from the close to 10% of IDH$^{mut}$ astrocytomas with non-IDH1-R132H mutations. Most importantly, the present invention shows that BCAT1 and BCAA metabolism provide the basis for the development of novel metabolism-based approaches in glioma therapy.

This means that suppression of BCAT1 in IDH$^{wt}$ glioblastomas has the potential to significantly impede tumor growth as well as the excretion of glutamate by the tumor cells, which frequently causes neurotoxicity to surrounding brain tissue and leads to tumor-associated epilepsy in brain tumor patients.

In addition, the data of the present invention show that availability of large amounts of glucose and glutamine, the two nutrients considered to be most important for supporting malignant cell growth, is not sufficient to support sustained fast growth of IDH$^{wt}$ glioblastoma.

In other words, in the present invention it has been shown that BCAT1 overexpression is a highly characteristic feature of glioblastoma, in particular IDH$^{wt}$ glioblastoma, and essential for their aggressive clinical behavior. Thus, BCAT1 expression and BCAA catabolism are promising markers for the diagnostic and prognostic assessment of gliomas and serve as novel therapeutic targets. Furthermore, the present invention represents the first example of silencing of a metabolic gene that is central to glioma pathomechanism by IDH1 mutation-associated aberrant DNA methylation. Silencing of BCAT1 early in tumor development will prevent IDH$^{mut}$ gliomas from utilizing BCAAs as a metabolic resource and offers an explanation for the less malignant growth behaviour of IDH$^{mut}$ gliomas relative to the BCAT1-dependent IDH$^{wt}$ glioblastomas.

The reduction, silencing or inhibition of the biological activity can be effected by direct interaction or binding of a compound to BCAT1 or by indirect interaction, e.g., by interacting with a compound that is associated with the biological activity of BCAT1. The reduction or inhibition of the biological activity can also be achieved by the application of altered, e.g., inactive forms of BCAT1, preferably in excess.

Examples of suitable compounds reducing, silencing or inhibiting the biological activity of BCAT1 or the expression of the gene encoding BCAT1 with the aim to get a therapeutic effect are:

(a) Plasmids, vectors or natural/synthetic/mutated viruses oligonucleotides of various types of modification (e.g. PTO, LNA, 2'F-ANA, protein-nucleotide complexes, RNA$_i$, siRNA or mikro$_{mi}$RNA, shRNA, Methylmethoxy-, Phosphoroamidates, PNA, Morpholino, Phosphoramidate, Cyclohexen (CeNA), gap-meres, ribozymes, aptamers, CpG-oligos, DNA-zymes, riboswitches, or lipids or lipid containing molecules;

(b) peptides, peptide complexes, including all types of linkers, (c) small molecules;

(d) antibodies and their derivatives, especially chimeras, Fab-fragments, Fc-fragments, or (e) carriers, liposomes, nanoparticles, complexes, or any other delivery systems containing the above named constructs, (f) oxidizing agents or sulfhydryl (SH groups) modifying agents.

Further compounds suitable for the purposes of the present invention and methods how to identify/select such compounds are in more detail described below.

Preferably, in a pharmaceutical composition, such compounds as described above are combined with a pharmaceutically acceptable carrier. "Pharmaceutically acceptable" is meant to encompass any carrier, which does not interfere with the effectiveness of the biological activity of the active ingredient and that is not toxic to the host to which it is administered. Examples of suitable pharmaceutical carriers are well known in the art and include phosphate buffered saline solutions, water, emulsions, such as oil/water emulsions, various types of wetting agents, sterile solutions etc. Such carriers can be formulated by conventional methods and the active compound can be administered to the subject at an effective dose.

An "effective dose" refers to an amount of the active ingredient that is sufficient to affect the course and the severity of the neoplasia, leading to the reduction or remission of such a pathology. An "effective dose" useful for treating and/or preventing neoplasias may be determined using methods known to one skilled in the art (see for example, Fingl et al., The Pharmocological Basis of Therapeutics, Goodman and Gilman, eds. Macmillan Publishing Co., New York, pp. 1-46 ((1975)).

Administration of the suitable compositions may be effected by different ways, e.g. by intravenous, intraperitoneal, subcutaneous, intramuscular, topical or intradermal administration. The route of administration, of course, depends on the kind of therapy and the kind of compound contained in the pharmaceutical composition. The dosage regimen will be determined by the attending physician and other clinical factors. As is well known in the medical arts, dosages for any one patient depends on many factors, including the patient's size, body surface area, age, sex, the particular compound to be administered, time and route of administration, the kind of therapy, general health and other drugs being administered concurrently.

The person skilled in the art can easily identify or generate compounds useful for the treatments of the present invention based on the knowledge of the amino acid sequence of BCAT1, and the nucleotide sequence of the gene encoding this protein. Respective sequences are found in the UniProtKB/Swiss-Prot database (P54687; BCAT1 HUMAN), in Genbank (NCBI Reference Sequence: NM_005504) and the Human Genome Organization Gene Nomenclature Committee (HGNC) database (HGNC ID: 976).

In a further preferred embodiment of the present invention the compound useful for reducing or inhibiting the expression of the gene encoding BCAT1 is an antisense oligonucleotide, shRNA or siRNA specific for BCAT1. Preferably, the compound useful for silencing the BCAT1 expression are independent Mission° shRNA constructs targeting different regions of the human BCAT1 (BCAT1 shRNAI NM005504.3-1064s1c1 and BCAT1 shRNAII NM_005504.3-751s1c1) and human IDH1 (IDH1 shRNAI NM_005896.2-1363s1c1 and IDH1 shRNAII NM_005896.2-292s1c1) mRNA transcripts.

The generation of suitable antisense oligonucleotides includes determination of a site or sites within the BCAT1 encoding gene for the antisense interaction to occur such that the desired effect, e.g., inhibition of the expression of the protein, will result. A preferred intragenic site is (a) the region encompassing the translation initiation or termination codon of the open reading frame (ORF) of the gene or (b) a region of the mRNA which is a "loop" or "bulge", i.e., not part of a secondary structure. If one or more target sites have been identified, oligonucleotides are chosen which are sufficiently complementary to the target, i.e., hybridize sufficiently well and with sufficient specificity, to give the desired effect. In the context of this invention, "hybridization" means hydrogen bonding, which may be Watson-Crick, Hoogsteen or reversed Hoogsteen hydrogen bonding, between complementary nucleoside or nucleotide bases. "Complementary" as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can make hydrogen bonds with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound does not need to be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., in the case of therapeutic treatment.

The skilled person can generate antisense compounds and siRNA or shRNAs according to the present invention on the basis of the known DNA sequence for BCAT1.

"Oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases. While antisense oligonucleotides are a preferred form of the antisense compound, the present invention comprehends other oligomeric antisense compounds, including but not limited to oligonucleotide mimetics such as are described below. The antisense compounds in accordance with this invention comprise from about 8 to about 50 nucleobases (i.e. from about 8 to about 50 linked nucleosides). Particularly preferred antisense compounds are antisense oligonucleotides, even more preferably those comprising from about 15 to about 25 nucleobases. Antisense compounds include ribozymes, external guide sequences (EGS), oligonucleotides (oligozymes), and other short catalytic RNAs or catalytic oligonucleotides which hybridize to the target nucleic acid and inhibit its expression.

Alternatively, the compound of the invention is a vector allowing to transcribe an antisense oligonucleotide of the invention, e.g., in a mammalian host. Preferably, such a vector is a vector useful for gene therapy. Preferred vectors useful for gene therapy are viral vectors, e.g. adenovirus, herpes virus, vaccinia, or, more preferably, an RNA virus such as a retrovirus. Even more preferably, the retroviral vector is a derivative of a murine or avian retrovirus. Examples of such retroviral vectors which can be used in the present invention are: Moloney murine leukemia virus (MoMuLV), Harvey murine sarcoma virus (HaMuSV), murine mammary tumor virus (MuMTV) and Rous sarcoma virus (RSV). Most preferably, a non-human primate retroviral vector is employed, such as the gibbon ape leukemia virus (GaLV), providing a broader host range compared to murine vectors. Since recombinant retroviruses are defective, assistance is required in order to produce infectious particles. Such assistance can be provided, e.g., by using helper cell lines that contain plasmids encoding all of the structural genes of the retrovirus under the control of regulatory sequences within the LTR. Suitable helper cell lines are well known to those skilled in the art. Said vectors can additionally contain a gene encoding a selectable marker so that the transduced cells can be identified. Moreover, the retroviral vectors can be modified in such a way that they become target specific. This can be achieved, e.g., by inserting a polynucleotide encoding a sugar, a glycolipid, or a protein, preferably an antibody. Those skilled in the art know additional methods for generating target specific vectors. Further suitable vectors and methods for in vitro- or in vivo-gene therapy are described in the literature and are known to the person skilled in the art; see, e.g., WO 94/29469 or WO 97/00957.

In order to achieve expression only in the target organ, e.g., a brain tumor, the DNA sequences for transcription of the antisense oligonucleotides can be linked to a tissue specific promoter and used for gene therapy. Such promoters are well known to those skilled in the art (see e.g. Zimmermann et al., (1994) Neuron 12, 11-24; Vidal et al.; (1990) EMBO J. 9, 833 840; Mayford et al., (1995), Cell 81, 891-904; Pinkert et al. (1987) Genes & Dev. 1, 268-76).

Within an oligonucleotide structure, the phosphate groups are commonly referred to as forming the internucleoside backbone of the oligonucleotide. The normal linkage or backbone of RNA and DNA is a 3' to 5' phosphodiester linkage. Specific examples of preferred antisense compounds useful in the present invention include oligonucleotides containing modified backbones or non-natural internucleoside linkages. Oligonucleotides having modified backbones include those that retain a phosphorus atom in the backbone and those that do not have a phosphorus atom in the backbone. Modified oligonucleotide backbones which can result in increased stability are known to the person skilled in the art, preferably such modification is a phosphorothioate linkage.

A preferred oligonucleotide mimetic is an oligonucleotide mimetic that has been shown to have excellent hybridization properties, and is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone (see, e.g., Nielsen et al., Science 254 (1991), 1497-1500.)

Modified oligonucleotides may also contain one or more substituted or modified sugar moieties. Preferred oligonucleotides comprise one of the following at the 2' position: OH; F; O—, S-, or N-alkyl; O—, S—, or N-alkenyl; O—S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. A particularly preferred modified sugar moiety is a 2'-O-methoxyethyl sugar moiety.

Oligonucleotides of the invention may also include nucleobase modifications or substitutions. Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine etc., with 5-methylcytosine substitutions being preferred since these modifications have been shown to increase nucleic acid duplex stability.

Another modification of the oligonucleotides of the invention involves chemically linking to the oligonucleotide one or more moieties or conjugates which enhance the activity, cellular distribution or cellular uptake of the oligonucleotide. Such moieties include lipid moieties such as a cholesterol moiety, cholic acid, a thioether, a thiocholesterol, an aliphatic chain, e.g., dodecandiol or undecyl residues, a phospholipid, a polyamine or a polyethylene glycol chain, or adamantane acetic acid, a palmityl moiety, or an octadecylamine or hexylamino-carbonyl-oxycholesterol moiety.

The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers.

In a further preferred embodiment of the present invention, the compounds for use in a method of treating a neoplasia are compounds reducing or inhibiting the biological activity of BCAT1.

Such compounds are described in the art for medical indications differing from the indication of the present invention and, preferably, comprise compounds like 1-(aminomethyl)cyclohexaneacetic acid (gabapentin) or a compound described in Goto et al., The Journal of Biological Chemistry 280(44) (2005), 37246-56, Hu et al., Bioorganic & Medicinal Chemistry Letters 16 (2006), 2337-40, Caballero et al., Molecular Diversity 13 (2009), 493-500, U.S. Pat. Nos. 6,632,831, 6,809,119, and EP-B1 1 157 000.

Further examples of compounds capable of reducing or inhibiting the biological activity of BCAT1 are (neutralizing) antibodies directed against BCAT1 or fragments thereof having substantially the same binding specificity. The term "antibody", preferably, relates to antibodies which consist essentially of pooled monoclonal antibodies with different epitopic specificities, as well as distinct monoclonal antibody preparations. Monoclonal antibodies are made from an antigen containing, e.g., a fragment of BCAT1 by methods well known to those skilled in the art (see, e.g., Köhler et al., Nature 256 (1975), 495). As used herein, the term "antibody" (Ab) or "monoclonal antibody" (Mab) is meant to include intact molecules as well as antibody fragments (such as, for example, Fab and F(ab')2 fragments) which are capable of specifically binding to protein. Fab and F(ab')2 fragments lack the Fc fragment of intact antibody, clear more rapidly from the circulation, and may have less non-specific tissue binding than an intact antibody. (Wahl et al., J. Nucl. Med. 24: 316-325 (1983)). Thus, these fragments are preferred, as well as the products of a FAB or other immunoglobulin expression library. Moreover, antibodies useful for the purposes of the present invention include chimerical, single chain, and humanized antibodies.

Alternatively, preferred compounds for the purpose of the invention are inactive versions of BCAT1 or nucleic acid sequences encoding inactive versions of BCAT1 that can be introduced according to the approaches/vectors described above. Such inactive versions can be generated according to well known methods of mutagenesis. Such compounds can have a therapeutic effect in the human body by displacing their functionally active counterpart, in particular when applied in excess. Analyses of potentially inactive versions of BCAT1 can be carried out by assaying the (reversible) transamination of branched-chain L-amino acids to branched-chain alpha-keto acids, e.g., by determining the production of glutamate. Suitable assays are described in the literature and, e.g., in Example 39 of U.S. Pat. No. 6,809,119, Hu et al. (2006), and EP-B1 1 157 000.

In a preferred embodiment of the present invention the compound described in detail above is used in a method of treating an astrocytic brain tumor or glioblastoma.

The present invention also relates to a method for identifying a compound reducing or inhibiting the biological activity of BCAT1 and/or its expression, comprising the steps of:
  (a) incubating a candidate compound with a test syste comprising BCAT1 or its gene; and
  (b) assaying a biological activity of BCAT1;
    wherein an inhibition or loss of a biological activity of BCAT1, preferably compared to a test system in the absence of said test compound, is indicative of the presence of candidate compound having the desired property.

Step (b) can be carried out by assaying the (reversible transamination of branched-chain L-amino acids to branched-chain alpha-keto acids using an assay as described above.

Examples of such candidate molecules include antibodies, oligonucleotides, proteins, or small molecules. Such molecules can be rationally designed using known techniques.

Preferably, said test system used for screening comprises substances of similar chemical and/or physical properties, most preferably said substances are almost identical. The compounds which can be prepared and identified according to a use of the present invention may be expression libraries, e.g., cDNA expression libraries, peptides, proteins, nucleic acids, antibodies, small organic compounds, ligands, hormones, peptidomimetics, PNAs or the like.

WO 98/25146 describes further methods for screening libraries of complexes for compounds having a desired property, especially, the capacity to agonize, bind to, or antagonize a polypeptide or its cellular receptor. The complexes in such libraries comprise a compound under test, a tag recording at least one step in synthesis of the compound, and a tether susceptible to modification by a reporter molecule. Modification of the tether is used to signify that a complex contains a compound having a desired property. The tag can be decoded to reveal at least one step in the synthesis of such a compound. Other methods for identifying compounds which interact with BCAT1 or nucleic acid molecules encoding such molecules are, for example, the in vitro screening with the phage display system as well as filter binding assays or "real time" measuring of interaction.

It is also well known to the person skilled in the art, that it is possible to design, synthesize and evaluate mimetics of small organic compounds that, for example, can act as a substrate or ligand to BCAT1. For example, it has been described that D-glucose mimetics of hapalosin exhibited similar efficiency as hapalosin in antagonizing multidrug resistance assistance-associated protein in cytotoxicity; see Dinh, J. Med. Chem. 41 (1998), 981-987.

All these methods can be used in accordance with the present invention to identify a compound reducing or inhibiting the biological activity of BCAT1 or its expression.

The gene encoding BCAT1 can also serve as a target for the screening of inhibitors. Inhibitors may comprise, for example, proteins that bind to the mRNA of the genes encoding BCAT1, thereby destabilizing the native conformation of the mRNA and hampering transcription and/or translation. Furthermore, methods are described in the literature for identifying nucleic acid molecules such as a RNA fragment that mimics the structure of a defined or undefined target RNA molecule to which a compound binds inside of a cell resulting in the retardation of the cell growth or cell death; see, e.g., WO 98/18947 and references cited therein. These nucleic acid molecules can be used for identifying unknown compounds of pharmaceutical interest, and for identifying unknown RNA targets for use in treating a disease. These methods and compositions can be used for identifying compounds useful to reduce expression levels of BCAT1.

The compounds which can be tested and identified according to the method of the invention may be expression libraries, e.g., cDNA expression libraries, peptides, proteins, nucleic acids, antibodies, small organic compounds, hormones, peptidomimetics, PNAs or the like (Milner, Nature Medicine 1 (1995), 879-880; Hupp, Cell 83 (1995), 237-245; Gibbs, Cell 79 (1994), 193-198 and references cited supra). Furthermore, genes encoding a putative regulator of BCAT1 and/or which exert their effects up- or downstream of BCAT1 may be identified using, for example, insertion mutagenesis using, for example, gene targeting vectors known in the art. Said compounds can also be functional derivatives or analogues of known inhibitors. Such useful compounds can be for example transacting factors which bind to BCAT1 or regulatory sequences of the gene encoding it. Identification of transacting factors can be carried out using standard methods in the art. To determine whether a protein binds to the protein itself or regulatory sequences, standard native gel-shift analyses can be carried out. In order to identify a transacting factor which binds to the protein or regulatory sequence, the protein or regulatory sequence can be used as an affinity reagent in standard protein purification methods, or as a probe for screening an expression library. The identification of nucleic acid molecules which encode polypeptides which interact with BCAT1 can also be achieved, for example, as described in Scofield (Science 274 (1996), 2063-2065) by use of the so-called yeast "two-hybrid system". In this system BCAT1 is linked to the DNA-binding domain of the GAL4 transcription factor. A yeast strain expressing this fusion polypeptide and comprising a lacZ reporter gene driven by an appropriate promoter, which is recognized by the GAL4 transcription factor, is transformed with a library of cDNAs which will express plant proteins or peptides thereof fused to an activation domain. Thus, if a peptide encoded by one of the cDNAs is able to interact with the fusion peptide comprising a peptide of BCAT1, the complex is able to direct expression of the reporter gene. In this way, BCAT1 and the gene encoding BCAT1 can be used to identify peptides and proteins interacting with BCAT1. It is apparent to the person skilled in the art that this and similar systems may then further be exploited for the identification of inhibitors.

The below example explains the invention in more detail but are not construed as a limitation of the invention.

EXAMPLE 1

General Methods (a) RNA Isolation and Quantitative Real-time PCR (qRT-PCR)

Total RNA was extracted using the AllPrep DNA/RNA/Protein Mini Kit (Qiagen) according to the manufacturer's instructions. FirstChoice® Human Brain Reference Total RNA from Ambion served as normal brain RNA pool (n=23 donors). Total RNA (500 ng) was reverse-transcribed using random primers and superscript II (Invitrogen, Karlsruhe, Germany) according to the manufacturer's instructions. Each complimentary DNA sample was analysed in triplicate with the Applied Biosystems Prism 7900HT Fast Real-Time PCR System (Applied Biosystems, Foster City, Calif., USA) using Absolute SYBR Green ROX Mix (ABgene, Epsom, UK). The relative amount of specific mRNA was normalised to ARF, B2M and TBP. Primer sequences are given in the following Table 1A.

TABLE 1A

| Expression primer | | | |
|---|---|---|---|
| BCAT1 (all isoforms) | Forward | CAACTATGGAGAAT GGTCCTAAGCT | SEQ ID NO: 1 |
|  | Reverse | TGTCCAGTCGCTCT CTTCTCTTC | SEQ ID NO: 2 |
| BCAT1 T1 (ENST00000261192) | Forward | GCTACGACCCTTGG GATCT | SEQ ID NO: 3 |
| BCAT1 T4 (ENST00000539282) | Forward | GTGCCACTGCCGCT CTCT | SEQ ID NO: 4 |

TABLE 1A-continued

Expression primer

| | | | |
|---|---|---|---|
| BCAT1 T6 (ENST00000538118) | Forward | TGGTTGTCTGAGCC TCCTTT | SEQ ID NO: 5 |
| BCAT1 Exon 2 | Reverse | AAGTCCCCACCACC TCTTTT | SEQ ID NO: 6 |
| BCAT1 Exon 5 | Reverse | CCCATTCTTGATCC AATTTCA | SEQ ID NO: 7 |
| HEY1 | Forward | CGAGCTGGACGAGA CCAT | SEQ ID NO: 8 |
| | Reverse | GAGCCGAACTCAAG TTTCCA | SEQ ID NO: 9 |
| ARF | Forward | GACCACGATCCTCT ACAAGC | SEQ ID NO: 10 |
| | Reverse | TCCCACACAGTGAA GCTGATG | SEQ ID NO: 11 |
| B2M | Forward | ACTGAATTCACCCC CACTGA | SEQ ID NO: 12 |
| | Reverse | CCTCCATGATGCTG CTTACA | SEQ ID NO: 13 |
| TBP | Forward | GAACCACGGCACTG ATTTTC | SEQ ID NO: 14 |
| | Reverse | CCCCACCATGTTCT GAATCT | SEQ ID NO: 15 |
| | Reverse | AAATAACTTAACAC CCCAATCTAAAC | SEQ ID NO: 16 |

(b) Western Blot Analysis

All experiments involving the use of human tissues are carries out in line with the guidelines of the institutional review board of the Medical Faculty at Heinrich Heine University Dusseldorf. Fresh frozen human tumor tissue samples and a non-neoplastic brain tissue sample were lysed in guanidine isothiocyanate solution (4M) using an ULTRA-TURRAX (IKA, Staufen, Germany) and subjected to CsCl-ultracentrifugation. Diafiltration of the obtained protein fractions was performed using the Amicon Ultra-0.5 centrifugal filter devices (Millipore, Schwalbach, Germany; 3 kDa cut-off) essentially as described[45]. Total protein of cell lines was extracted using the AllPrep DNA/RNA/Protein Mini kit (Qiagen). 10 μg of protein were separated by 10% SDS-PAGE and transferred to PVDF membranes (Millipore). The membrane was blocked in blocking solution (5% BSA in TBS, 0.1% Tween 20) and incubated with primary antibodies overnight at 4° C. Horseradish peroxidase (HRP)-conjugated secondary antibodies were incubated for 1 hour at room temperature prior to the chemiluminescent detection of protein (ECL kit; GE Healthcare, Little Chalfont, UK).

The following antibodies were used: monoclonal mouse antibody against α-tubulin (1:2000, #T9026, Sigma-Aldrich, St. Louis, Mo. 63178, USA), monoclonal mouse antibody against BCAT1 (1:2000, ECA39, clone 51, #611270, BD Biosciences, San Jose, Calif., USA), monoclonal rat antiserum against IDH1 (1:1, provided by A. von Deimling, DKFZ, Heidelberg, Germany; commercially available from Dianova, Hamburg, Germany), monoclonal mouse antibody against HADHSC (1:500, #H00003033-M01, Abnova) monoclonal rabbit antibody against CDKN1B (1:1000, p27 Kip1, #3686, Cell Signaling Technology), monoclonal rabbit antibody against Akt (1:1000, #9272, Cell Signaling Technology), monoclonal rabbit antibody against phospho-Akt (Ser473) (1:1000, #193H12, Cell Signaling Technology), polyclonal rabbit antibody against p70 S6 kinase (1:1000, #9202, Cell Signaling Technology), polyclonal rabbit antibody against phospho-p70 S6 kinase (Thr389) (1:1000, #9205, Cell Signaling Technology), HRP-conjugated anti-rat IgG (1:10000, provided by A. von Deimling, DKFZ, Heidelberg, Germany), HRP-conjugated horse anti-mouse IgG (1:5000, #7076, Cell Signaling Technology), HRP-conjugated goat anti-rabbit IgG (1:2000, #7074, Cell Signaling Technology).

(c) Immunohistochemical Staining

Tumor sections were deparaffinised using xylol and rehydrated in decreasing concentrations of ethanol. Antigen retrieval was performed by heating for 40 min in a steamer in 10 mM sodium citrate buffer (pH 6.0). Endogenous peroxidase was inactivated by incubating the tumor sections in 3% hydrogen peroxide. Sections were incubated overnight with primary anti-BCAT1 (ECA39) monoclonal mouse antibody, clone 51 (BD Biosciences, San Jose, Calif.) diluted 1:500 or mouse anti-human IDH1 R132H antibody (Dianova, Hamburg, Germany) diluted 1:20 in Dako REAL™ antibody diluent (Dako, Glostrup, Denmark). Staining for detection of bound antibody was performed according to standard protocols using the EnVision™ detection system (peroxidase/DAB+, rabbit/mouse) (Dako, Glostrup, Denmark), subsequent counterstaining was done using hematoxylin.

(d) DNA Methylation Analysis

DNA methylation was analyzed by MassARRAY technique. Briefly, 500 ng genomic DNA was chemically modified with sodium bisulfite using the EZ methylation kit (Zymo Research) according to the manufacturer's instructions. The bisulfite-treated DNA was PCR-amplified with primers generating four amplicons (A1-A4) from −990 by to +612 by around TSS of BCAT1 transcript 1 (Ti, ENST00000261192), and three amplicons (A5-A7) of the promoter of BCAT1 transcript 4 (T4 , ENST00000539282) and 6 (T6, ENST00000538118) from −198 bp to +63 bp. The amplicons were transcribed by T7 polymerase, followed by T specific-RNAaseA cleavage. The digested fragments were quantified by mass-spectrometry. The primer sequences are given in Table 1B. DNA methylation standards (0%, 20%, 40%, 60%, 80%, and 100% methylated genomic DNA) were used to confirm the unbiased amplification of the amplicons.

TABLE 1B

Methylation analysis primer

| | | |
|---|---|---|
| A1 * | Forward | AAGTTTTTGTTGTGGAAGTTGTTTT |
| | Reverse | CACCTAACCAACAATCATTAAACACTA |
| A2 * | Forward | TTTGTTTGAGGGTATTGGAAGTAAT |
| | Reverse | TAACTCCTACCCACCTCCCTACTAT |
| A3 * | Forward | ATAGTAGGGAGGTGGGTAGGAGTTA |
| | Reverse | AAACACTAAAACTACTCCCCCAAAC |
| A4 * | Forward | GTTTGGGGGAGTAGTTTTAGTG |
| | Reverse | CTCCCTACCAACTATATTTCTTA |
| A5 * | Forward | ATTTATGAGGGTGTTAGATTTGGGT |
| | Reverse | TTAAAAACTCCTCCCCAAAAAATAC |
| A6 * | Forward | TTGTTTAGGTTTAGTATTTTTATGGG |
| | Reverse | ACCATTTATAAAAAAATCTCCAAAA |
| A7 * | Forward | AAATTATTATTAAGTAAATGTAGGTGGG |

(e) Cell culture

The human glioma cell lines U-87MG (HTB-14), LN-229 (CRL-2611), Hs683 (HTB-138) and U-373MG (HTB-17) were cultured in Dulbecco's Minimal Essential Medium (DMEM) supplemented with 10% fetal calf serum and 1% penicillin/streptomycin-mix. Cell lines were authenticated by short tandem repeat (STR) analysis. The brain cancer stem-like cells NCH421k were established from primary glioblastoma patients undergoing surgical resection according to the research proposals approved by the institutional review board at the Medical Faculty, University of Heidelberg. They were characterized genotypically and phenotypically in a previous study (Campos, B., et al. Differentiation therapy exerts antitumor effects on stem-like glioma cells. *Clin Cancer Res* 16, 2715-2728 (2010)) NCH421k cells were grown as floating aggregates (neurospheres) on uncoated tissue culture dishes in DMEM/ F-12 medium containing 20% BIT serum-free supplement, basic fibroblast growth factor and epidermal growth factor at a concentration of 20 ng/ml each (all from Provitro, Berlin, Germany). HEK293T and HEK293 cells were maintained as monolayer cultures in DMEM containing 10% fetal calf serum without antibiotics.

All cell lines were cultivated at 37° C. in a humidified incubator with 5% $CO_2$. For hypoxia experiments, cells were cultured at 1% $O_2$ in a nitrogen-supplied C16 hypoxia incubator (Labotect, Goettingen, Germany).

(f) Chromatin Immunoprecipitation (ChIP)

ChIP was performed on HEK293 cells overexpressing flag-tagged HEY1, since the currently available antibodies against HEY1 were not specific for ChIP assays. Constructs for HEY1 overexpression were prepared using gateway compatible vectors tagged with FLAG; pDest26 (C-terminal tag) and pDest11 (N-terminal tag). 1 µg of either the control vectors or HEY1 expression vectors were transfected into $2.5 \times 10^6$ HEK293 cells per 15 cm plate using TransIT®-LT1 (Mirus Bio LLC, Madison, Wis. 53711, USA) according to slightly modified manufacturer's instructions. The cells from two plates were harvested 48 hours after transfection. Chromatin was prepared using non-ionic shearing buffers with Covaris S2, according to the manufacturer's protocol (Covaris Inc.). ChIP was performed using anti-FLAG antibody (Cell signaling #2368). The DNA recovered after ChIP was used for qRT-PCR with input chromatin and mock immunoprecipitation (anti-IgG antibody, Diagenode, Kch-803-015) serving as controls. qRT-PCR was performed in triplicate with SYBR green detection using primers listed in Table 2. Ratios of bound to input signals are reported.

TABLE 2

| Promoter primer | | | | |
|---|---|---|---|---|
| PTPRD | Forward | GAGGAGGAGGAGAAAGAGCA | SEQ ID NO: | 30 |
| | Reverse | GACAGAGCCTCGCCTCCT | SEQ ID NO: | 31 |
| BCAT1_neg | Forward | TCCCTAGTCCTCCGTTCTGA | SEQ ID NO: | 32 |
| | Reverse | ATTCCAAGGAGCATTTGTGC | SEQ ID NO: | 33 |
| BCAT1_DMR (c1) | Forward | GAGGGTGACTAAGGAACTCTGG | SEQ ID NO: | 34 |
| | Reverse | ATTGCCATTCCGTCATCACT | SEQ ID NO: | 35 |
| BCAT1_c2 | Forward | GCTACGACCCTTGGGATCT | SEQ ID NO: | 36 |
| | Reverse | TCGATTCACGCACACATTTT | SEQ ID NO: | 37 |
| BHLHA15 | Forward | CCGAGGGCTCATTTGCAT | SEQ ID NO: | 38 |
| | Reverse | CACCCGAGTTCCCAGCTC | SEQ ID NO: | 39 |

(g) Transient Transfection of siRNA

HEK293T cells were transfected with siRNA duplexes from Ambion (HEY1: s23868-70) or Dharmacon (control non-targeting: D-001810-10) using DhamaFect1 following slight modifications to the manufacturer's instructions (Dharmacon). Briefly, each siRNA pool was diluted in 1× siRNA buffer (Dharmacon), was mixed with RPMI, and then distributed into 6 wells of 96 well plates. $1.2 \times 10^4$ HEK293 or $9 \times 10^3$ HEK293T cells were seeded on top of the siRNA/DharmaFECT mixture (the volume was 15 µl/well and 20 nM of siRNAs in final). After 48 hours incubation at 37° C., RNAs were isolated from the wells for further analysis.

(h) Virus Production and Transduction

Lentiviral vectors were produced by cotransfection of HEK293T cells with the psPAX2 (Addgene 12260, Didier Trono, packaging vector), pMD2.G (Addgene 12259, Didier Trono, envelope plasmid), and pLKO.1 shRNA constructs (Sigma-Aldrich) Transfections were carried out using TransIT™-LT1 (Mirus Bio LLC) and virus was harvested at 48 and 72 hours after transfection and combined.

Infection of glioma cells with virus at an M.O.I. of 2 was carried out in the presence of 8 µg/ml of polybrene (Chemicon, Billerica, Mass., USA). Virus-containing supernatant was removed after 24 hours and cells were split on day 3, day 5 and day 7 after transduction. Two independent Mission® shRNA constructs targeting different regions of the human BCAT1 (BCAT1 shRNAI NM_005504.3-1064s1c1 and BCAT1 shRNAII NM_005504.3-751s1c1) and human IDH1 (IDH1 shRNAI NM005896.2-1363s1c1 and IDH1 shRNAII NM_005896.2-292s1c1) mRNA transcripts were used. Nontargeting shRNA (Mission SHC002) was used as a control. Quantification of BCAT1 and IDH1 knockdown was assessed by quantitative real-time PCR and Western blot.

(i) Treatment with dimethyl-α-ketoglutarate and Gabapentin $5 \times 10^4$ cells/well were seeded in 24-well plates in a total volume of 500 µl cell culture medium. The medium was removed 16 hours after seeding the cells, and replaced with 500 µl medium containing 5 mM or 10 mM dimethyl-α-ketoglutarate (Dimethyl 2-oxoglutarate; Sigma-Aldrich) or 5 mM, 10 mM or 20 mM gabapentin (1-(Aminomethyl)-cyclohexane; Sigma-Aldrich). Corresponding volumes of 200 mM HEPES buffer (pH 7.4) were added to the respective control wells.

(j) Cell-cycle Analysis and Detection of Apoptosis

Cell-cycle analysis was performed 20 hours after treatment with gabapentin and 6 days after lentiviral transduction. Nicoletti buffer (0.1% sodium citrate, pH7.4, 0.05% Triton X-100, 50 µg propidium iodide) was added to the wells containing both dead and living cells. After 4 hours in the dark at 4° C., DNA content was analysed by flow cytometry using FACS Canto II (BD Biosciences, San Jose, Calif., USA). FACS Diva software was used to quantify the distribution of cells in each cell-cycle phase: sub-G1 (dead cells), G1, S, and G2/M. For investigation of apoptotic activity after lentivira knockdown NCH421k cells were incubated with annexin V-P (Phycoerythrin) and 7-AAD (7-aminoactinomycin D, BD Biosciences) for 15 minutes in the dark, immediately followed by flow cytometry.

(k) Proliferation Analysis

To assess the proliferation of glioma cells after treatment with gabapentin or after lentiviral knockdown, the Click-iT® EdU cell proliferation assay (Invitrogen, Karlsruhe, Germany) was used following the manufacturer's instructions. The cells were incubated with 10 µM of the nucleoside analog EdU (5-ethynyl-2'deoxyuridine) for 16 hours. Quantification of cells that incorporated EdU was performed using FACS Canto II (BD Biosciences).

(l) Glutamate Quantification

Glutamate concentration in the supernatant of cells treated with gabapentin was determined using the glutamine/glutamate determination Kit (GLN-1; Sigma-Aldrich)

according to the manufacturer's instructions. The reaction volumes were scaled down to 100 µl total volume and absorbance was measured in triplicate in a microplate (Corning° 96 Well Clear Flat Bottom UV-Transparent Microplate) using a Tecan Infinite M200 plate reader (Tecan, Austria). Data were normalised to the number of cells per well.

(m) Immunofluorescence Staining

Cells were plated on glass coverslips five days after lentiviral transduction. Cells were fixed in 4% formaldehyde, rinsed twice in 1× PBS, and permeabilized in PBS containing 0.2% Triton. Following rinsing with 1×PBS cells were incubated in 10% goat serum for 30 minutes at room temperature. Samples were incubated 1 hour with the primary antibody (mouse anti α-tubulin antibody, 1:200, #T9026, Sigma-Aldrich) and 1 hour at room temperature with the secondary antibody (FITC-conjugated goat anti mouse antibody, 1:100, ab6785, Abcam) following Mounting with DAPI-containing Vectashield mounting medium (Vector Laboratories, Burlingame, Calif., USA). For fluorescence imaging, images were taken using 40× objective lense on a Zeiss Axioplan microscope.

(n) 3D Microchannel Migration Assay

Poly(dimethylsiloxane) (PDMS) based microchannel chips were kindly provided by Dr. Ralf Kemkemer (Max Planck Institute for Intelligent Systems, Germany). Microfabricated channel structures with the dimensions of 5×11× 300 µm (W×H×L) were bio-functionalized by incubation with a 50 µg/ml fibronectin solution prior to use. The chip was fixed on a Teflon holder and $2 \times 10^5$ cells were seeded on the chip in close proximity to the channels. After cells were attached on the chip, live-cell imaging was performed for 25 hours. During the experiments no chemical gradient or flow inside the channels was applied. Phase-contrast time-lapse pictures of multiple positions were captured every 10 minutes with an automated invertd microscope (Zeiss Cell Observer; Carl Zeiss) equipped with an air-humidified and heated chamber. Images were recorded and processed with Zeiss AxioVision and ImageJ software. Cell behaviors were analyzed and categorized as reported previously (Bai, A. H., et al. MicroRNA-182 promotes leptomeningeal spread of nonsonic hedgehog-medulloblastoma. *Acta Neuropathol* (2011); Rolli, C. G., Seufferlein, T., Kemkemer, R. & Spatz, J. P. Impact of tumor cell cytoskeleton organization on invasiveness and migration: a microchannel-based approach. *PLoS One* 5, e8726 (2010)).

(o) Animal Experiments

Animal work was approved by the governmental authorities (Regierungspraesidium Karlsruhe, Germany) and supervised by institutional animal protection officials in accordance with the National Institutes of Health guidelines *Guide for the Care and Use of Laboratory Animals*.

(p) Orthotopic Brain Tumor Model

A total of $2 \times 10^5$ U-87MG cells with BCAT1 shRNAI knockdown or nontargeting shRNA were stereotactically implanted into the brain of six 7-9-week-old athymic mice (CD1 nu/nu; Charles River Laboratories, Wilmington, Mass., USA), respectively. Four weeks after implantation, animals were sacrificed, brains removed and cryosectioned. Brain sections were stained with hematoxylin and eosin and the tumor volume was calculated using ImageJ.

(q) Perchloric Acid Cell Extraction and NMR Spectroscopy

Cells were harvested by trypsinization, washed once with ice-cold PBS, and the cell pellet was frozen at −80° C. Typically $1 \times 10^8$ harvested cells were subjected to perchloric acid extraction followed by KOH neutralization according to published protocols[50]. Briefly, 2 mL of ice-cold 1 N $HClO_4$ were added to a frozen pellet of harvested cells. The pellet was disrupted using a Teflon pestle and a glass homogeniser. 1 mL of ice-cold water was added to the lysate, vortexed for 90 s and centrifuged at 10000×g for 10 min at 4° C. The pellet was re-extracted and the supernatants were combined. The extract was neutralised with KOH and the pH was adjusted to 6.5-7.0 Precipitated $KClO_4$ was pelleted at 25000×g for 20 min and the supernatant was lyophilised.

The lyophilised extract residues were dissolved in 0.5 ml of a $D_2O$ buffer (99.9% D) containing 30 mM sodium phosphate and 0.1 mM sodium azide (pH 7.02). For quantitative analysis a reference capillary (1.5 mm OD, 0.99 mm ID) was filled with a solution of 11 mM trimethylsilyl-2,2,3,3-tetradeuteropropanoic acid (TSP, sodium salt) in the $D_2O$ buffer described above. Subsequently, the capillary was sealed in the flame of a Bunsen burner. A calibration solution was prepared by placing weighed amounts of glucose and citric acid in the $D_2O$ buffer to give the calculated concentrations of 10.49 mM glucose and 4.95 mm glucose. $^1$H-NMR spectra of the calibration solution+capillary were acquired at 600 MHz (Avance AV-600, Bruker BioSpin GmbH) using a standard 5-mm NMR tube and a triple-resonance inverse probe under the same conditions to be used for the extracts (20° C., presaturation of residual HDO signal, repetition time TR=7 s, 30° flip angle). The signal integrals for citrate and glucose were set to values corresponding to the concentrations given above, and the integral of the TSP methyl signal was found to be equivalent to 4.60±0.10 mM protons. Cell extracts were measured with the calibrated reference capillary inserted (512 transients in 1 hour), and the $^1$H-NMR signals for the branched-chain amino acids, various metabolites, and the TSP reference were integrated. The TSP integral was defined as 4.60 mM so that the metabolite signal integrals gave directly the metabolite concentrations in mM (µmol/ml) for the 0.5 ml volumes used. These data were then converted to femtomol/cell using the cell counts determined prior to extraction.

(r) Preparation of cell homogenates

Cell pellets were diluted in 100 µl water and homogenized by sonification (Ultrasonic device, 3-5×20 cycle, output 80% Branson Sonifier 450, Dietzenbach, Germany). Protein was determined according to Lowry (Lowry, O.H., Rosebrough, N.J., Farr, A. L. & Randall, R. J. Protein measurement with the Folin phenol reagent. *J Biol Chem* 193, 265-275 (1951) with the modifications of Helenius and Simons (Helenius, A. & Simons, K. The binding of detergents to lipophilic and hydrophilic proteins. *J Biol Chem* 247, 3656-3661 (1972)) using bovine serum albumin as a standard. The final protein concentrations of the homogenates should be in a range of 2-4 mg/ml. These dilutions were used for all analyses.

(s) Statistical Analysis

The relationship between IDH1/IDH2 mutation status and BCAT1 protein expression (FIG. 1k) was tested with the two-sided Fisher's Exact Test. The Student' t test (two-tailed, unpaired) was used for all other statistical comparisons. *, P<0.05; , P<0.01; *, P<0.001.

EXAMPLE 2

Inhibition of the Cell Proliferation by Gabapentin

The human glioblastoma cell lines U87-MG (HTB-14), HS683 (HTB-138) and U373-MG (HTB-17; LGC Standards, Teddington TW11 0LY U.K.) were cultured in Dulbecco's Minimal Essential Medium supplemented with 10% fetal calf serum and 1% penicillin/streptomycin-mix. $5 \times 10^4$ cells/well were seeded in 24 well plates in a total volume of 500 µl cell culture medium. The medium was removed 4 hours after seeding the cells, and replaced with 500 μl medium containing 1-(Aminomethyl)-cyclohexylessigsäure (Gabapentin, dissolved in 200 mM HEPES buffer at a concentration of 500mM) at final concentrations of 5 mM, 10 mM and 20 mM, respectively. Corresponding volumes of 200 mM HEPES were added to the respective control wells. 5 hours after exchanging the medium, 5-ethynyl-2'-deoxyuridine (EdU; Carlsbad, Calif. 92008, USA) was added in order to measure cell proliferation using Invitrogens (Carlsbad, Calif. 92008, USA Click iT® proliferation kit. The cells were harvested 16 hours after EdU application and proliferation was measured according to the manufacturer's instructions using a BD Biosciences FACS Canto II flow cytometer (BD Biosciences, Franklin Lakes, N.J. USA 07417). Three replicate measurements were obtained for each treatment. In all cell lines a concentration-dependent significant reduction of cell proliferation of about 20-55% was observed in the gabapentin treated cells as compared to mock treated cells. The results are shown in FIG. 10.

EXAMPLE 3

Inhibition of the Cell Proliferation by BCAT1 Antisense Oligonucleotides

Lentiviral vectors were produced by the cotransfection of HEK293T cells with the psPAX2 (Addgene 12260, Didier Trono, packaging vector), pMD2.G (Addgene 12259, Didier Trono, envelope plasmid), and pLK0.1 shRNA constructs (Sigma-Aldrich, St. Louis, Mo. 63178, USA). Transfections were carried out using TransIT®-LT1 (Mirus Bio LLC, Madison, Wis. 53711, USA) and virus was harvested at 48 and 72 hours after transfection. Two independent shRNA constructs targeting different regions of the BCAT1 mRNA transcript were used: MISSION shRNA TRCN0000005907 NM_005504.3-1064s1c1 (shRNA1) and TRCN0000005909 NM_005504.3-751s1c1 (shRNA2); all Sigma-Aldrich, St. Louis, Mo. 63178, USA. Nontargeting shRNA was used as a control.

The human glioblastoma cell lines U87-MG (HTB-14), HS683 (HTB-138) and U373-MG (HTB-17; LGC Standards, Teddington TW11 0LY, U.K.) were seeded in 24 well plates (5×104 cells/well) in a total volume of 500 μl cell culture medium. After 24 hours cells were transduced with virus in the presence of 8 μg/ml of polybrene. Virus-containing supernatant was removed after 24 hours and cells were split on day 3 and day 5 after transduction. Decreased BCAT1 mRNA and protein expression was detected using quantitative real-time PCR and Western blot (ECA39 antibody, BD Biosciences Pharmingen, San Diego, Calif. 92121, USA). A proliferation assay was carried out on day 6 using the Click-iT®) EdU cell proliferation kit after incubating cells with 10 μM EdU for 16 hours. In all of the BCAT1 shRNA transduced cells a reduction of proliferation was observed ranging from 20-80% depending on the cell line. These results are shown in FIG. 11.

EXAMPLE 4

Determination of BCAT1 Overexpression in IDH$^{wt}$ Glioblastomas

Prediction analysis of microarrays on gene expression data from astrocytic gliomas of WHO grades II, III and IV identified BCAT1 as the best classifier distinguishing primary glioblastoma from other astrocytoma as can be seen in the following Table 3:

| Rank | Gene symbol | AII$_{13}$ AAIII_sGBIV-score | pGBIV-score |
|---|---|---|---|
| 1 | BCAT1 | −0.530 | 0.435 |
| 2 | CHI3L1 | −0.503 | 0.413 |
| 3 | TIMP1 | −0.492 | 0.404 |
| 4 | IGFBP2 | −0.453 | 0.372 |
| 5 | PDPN | −0.448 | 0.368 |
| 6 | SERPINE1 | −0.442 | 0.363 |
| 7 | EMP3 | −0.436 | 0.358 |
| 8 | ADM | −0.413 | 0.338 |
| 9 | PTX3 | −0.403 | 0.331 |
| 10 | COL6A2 | −0.399 | 0.327 |
| 11 | NNMT | −0.396 | 0.325 |
| 12 | LIF | −0.393 | 0.323 |
| 13 | STEAP3 | −0.371 | 0.304 |
| 14 | COL6A2 | −0.371 | 0.304 |
| 15 | POSTN | −0.361 | 0.296 |
| 16 | KCNE4 | −0.359 | 0.295 |
| 17 | ABCC3 | −0.348 | 0.286 |
| 18 | FABP5 | −0.343 | 0.282 |
| 19 | LOX | −0.342 | 0.281 |
| 20 | RANBP17 | 0.339 | −0.278 |
| 21 | MOXD1 | −0.337 | 0.276 |
| 22 | ADAM12 | −0.336 | 0.276 |
| 23 | RBP1 | −0.331 | 0.272 |
| 24 | OCIAD2 | −0.330 | 0.270 |
| 25 | SAA2 | −0.320 | 0.263 |
| 26 | FMOD | −0.319 | 0.262 |
| 27 | PBEF1 | −0.317 | 0.260 |
| 28 | ATP7B | −0.316 | 0.259 |
| 29 | SOCS3 | −0.315 | 0.259 |
| 30 | PLAT | −0.314 | 0.258 |
| 31 | RARRES2 | −0.312 | 0.256 |
| 32 | RAB34 | −0.305 | 0.250 |
| 33 | VEGF | −0.304 | 0.249 |
| 34 | RBP1 | −0.303 | 0.249 |
| 35 | SAA1 | −0.302 | 0.248 |
| 36 | NA | 0.300 | −0.246 |
| 37 | PCDH15 | 0.296 | −0.243 |
| 38 | AL354720.14 | −0.293 | 0.240 |
| 39 | PBEF1 | −0.291 | 0.239 |
| 40 | EFEMP2 | −0.291 | 0.238 |
| 41 | IL8 | −0.288 | 0.236 |
| 42 | UPP1 | −0.284 | 0.233 |
| 43 | ANXA2 | −0.282 | 0.231 |
| 44 | TNFRSF12A | −0.279 | 0.229 |
| 45 | ANGPT2 | −0.273 | 0.224 |
| 46 | ANXA2 | −0.272 | 0.224 |
| 47 | EMILIN2 | −0.272 | 0.223 |
| 48 | TMEM158 | −0.268 | 0.220 |
| 49 | VEGF | −0.262 | 0.215 |
| 50 | PHYHIPL | 0.262 | −0.215 |

When classifying tumors based on IDH-mutation status, BCAT1 mRNA expression levels were significantly higher for IDH$^{wt}$ gliomas relative to IDH$^{mut}$ gliomas (FIG. 1b; P<0.0001; two-tailed Student's t-test), whereas comparably enhanced levels were not observed for BCAT2 expression (FIG. 1c; P=0.0301). Pathway analysis showed that, in addition to BCAT1, the RNA expression of several other genes of the BCAA catabolic pathway was upregulated in IDH$^{wt}$ compared to IDH$^{mut}$ tumors (FIG. 7). Consistent with the RNA expression results, Western blot analysis showed BCAT1 protein expression was high in IDH$^{wt}$ tumors, but essentially absent in IDH$^{mut}$ tumors, regardless of the specific mutation in either IDH1 or IDH2 (FIG. 1d). Sequencing of both the promoter and coding regions of BCAT1 for 20 gliomas revealed neither nonsense nor putative activating mutations. The observed tight correlation between IDH1 or IDH2 mutation and BCAT1 expression was further confirmed through immunohistochemical staining of sections from 81 primary human gliomas (77 astrocytoma, 4 oligodendroglioma), among which 45 of 46 IDH$^{wt}$ tumors showed strong BCAT1 staining (FIG. 1e), while 35 of 35 tumors with mutations in IDH1 (30 R132H, 1 R132C, 1 R132S) or IDH2 (3 R172K)

were BCAT1 negative (Fig. if-h); (P<0.0001; Fisher's Exact Test; FIG. 1k). The BCAT1 staining pattern therefore is largely complementary to the pattern obtained with the widely used antibody against the IDH1-R132H mutant protein (FIG. 1i,j). However, unlike IDH1-R132H staining, the BCAT1 antibody also distinguishes IDH$^{wt}$ tumors (FIG. 1e) from tumors with less common IDH1 and IDH2 mutations that are not recognized by anti-IDH1-R132H (Fig 1g-h). These data show that high BCAT1 expression is a characteristic feature of IDH$^{wt}$ gliomas that can be used to positively identify these tumors in a diagnostic setting.

EXAMPLE 5

Determination of Substrate-Dependent Expression of BCAT1

BCAT1 was found to be expressed strongly in the glioblastoma cell lines LN-229, U-87MG, U-373MG and to a lesser extent in A172 (FIG. 2a), all of which were confirmed to carry IDH1 and IDH2 wildtype genes. BCAT1 expression also was elevated in the Hs683 cell line, which was originally derived from an oligodendroglioma but nevertheless displays an IDH$^{wt}$ genotype. Thus, all these cell lines can be considered suitable models for studying BCAT1 function. BCAT1 RNA and protein expression were upregulated under hypoxic conditions, which are frequently present in glioblastoma (FIG. 2b). BCAT1 expression correlated with the concentration of the substrate alpha-KG and was upregulated after increasing the concentration of cell-permeable dimethyl-alpha-KG-substrate in the culture medium (FIG. 2c). Conversely, shRNA-mediated knockdown of IDH1, a major source of alpha-KG in the cytoplasm, led to strong downregulation of BCAT1 expression (FIG. 2d).

EXAMPLE 6

Differentially Regulated BCAT1 Expression through DNA-Methylation in Two Alternative Promoters To further elucidate the differential regulation of BCAT1 expression in IDH$^{wt}$ and IDH$^{mut}$ gliomas, transcript expression in patient samples was quantified. Using RT-PCR and sequencing, expression of three protein-coding BCAT1 transcripts listed in the Ensembl database in IDH$^{wt}$ astrocytic primary tumors as well as in a pool of 23 normal brain tissues (FIG. 9) were confirmed. These three transcripts (T1, T4 and T6) encode proteins of 386, 398, and 385 amino acids, all three of which correspond to the single protein band of 43 kD as identified by Western blot analysis. These transcripts originate from two alternative promoters (FIG. 3a) and differ only in their first exons, which encode 2, 14 and 1 amino acid(s) in T1, T4 and T6, respectively. Transcript-specific qRT-PCR identified T6 as the predominant transcript representing 73% of all BCAT1 mRNA in primary tumors (FIG. 3b). Notably, expression of all BCAT1 transcripts was significantly higher in IDH$^{wt}$ compared to IDH$^{mut}$ tumors.

To investigate the possible mechanisms of BCAT1 transcriptional regulation, quantitative DNA methylation analysis on astrocytomas of all grades using MassARRAY analysis of PCR products amplified from bisulfite-treated DNA covering the two alternative promoters (FIG. 3c) were performed. Distinct methylation patterns were observed for IDH$^{wt}$ and IDH$^{mut}$ tumors. The major promoter (promoter 2) was hypermethylated in IDH$^{mut}$ tumors but mostly unmethylated in IDH$^{wt}$ tumors and normal brain (FIG. 3c, right panel). The average degree of methylation of the A6 and A7 amplicons was strongly associated with IDH1 mutation status (FIG. 3d). These data show the suppression of transcripts T4 and T6 by promoter-2 methylation in IDH$^{mut}$ tumors. Promoter 1 (FIG. 3c, left panel) was mostly unmethylated in all tumor samples as well as in normal brain, with the exception of a stretch of hypermethylated sequences immediately upstream of the CpG island. Within this upstream region, three differentially methylated CpG-dinucleotides between IDH$^{wt}$ and IDH$^{mut}$ tumors at positions −699/−697 (CpG4;5) and −660 (CpG6) in amplicon A2 were identified. In contrast to the methylation pattern in promoter 2, CpG4;5 (FIG. 3e) and CpG6 (FIG. 3f) showed significantly less methylation in IDH$^{mut}$ than in IDH$^{wt}$ tumors. The degree of methylation in this differentially methylated region (DMR) correlated with the expression of the BCAT1 transcript Ti in IDH$^{wt}$ tumors supporting its functional relevance (FIG. 3g). The observed CpG-specific methylation pattern is consistent with repressor binding to the DMR leading to the downregulation of T1. Binding of the repressor HEY1 to the BCAT1 promoter 1 but not promoter 2 (FIG. 3a) previously had been suggested by ChIPseq data. Analysis of RNA expression data confirmed overexpression of the HEY1 repressor in astrocytic tumors compared to normal brain. Consistent with HEY1-repressor activity, siRNA-mediated HEY1 knockdown in HEK293T cells increased transcript-T1 expression (FIG. 3h,i). ChIP analysis demonstrated that compared to an upstream control region and to a region close to the translation start site, the strongest binding of two different HEY1 constructs occurs in the DMR (FIG. 3j,k). Together, these data strongly show differential expression of BCAT1 transcripts in astrocytomas is regulated by DNA methylation involving broad methylation of promoter 2 in IDH$^{mut}$ tumors and CpG-site specific methylation in a HEY1-repressor binding site in promoter 1 of IDH$^{wt}$ tumors.

EXAMPLE 7

Reduction of the Release of Glutamate by Glioblastoma Cells through the Suppression of BCAT1

To gain insight into the BCAT1 functional role in glioblastomas, cell lines U-87MG and U-373MG cell lines were treated with gabapentin, a leucine analog that specifically inhibits BCAT1, but not BCAT2. $^1$H-NMR spectroscopy of extracts of cells treated with 20 mM gabapentin for 20 hours demonstrated the intracellular accumulation of BCAAs, consistent with BCAT1 inhibition (FIG. 4ab). Glioblastoma release high concentrations of glutamate which leads to neuronal death by an excitotoxic mechanism. Glutamate release was significantly reduced with inhibition of BCAT1 with gabapentin (FIG. 4c) indicating that BCAT1 is a major contributor to glutamate production through BCAA catabolism in IDH$^{wt}$ glioma.

To independently confirm these findings, shRNA-mediated BCAT1 knockdown in U-87MG, U-373MG and Hs683 cells using two shRNAs that both target all three BCAT1 transcripts was performed. Tandem-MS analysis of the U-87MG cell culture media after 24 hour incubation revealed that glutamate release, as well as BCAA uptake were reduced in BCAT1 knockdown cells compared to control cells (FIG. 4d). A significant increase in release of alanine, glycine and threonine was also observed. Quantification of intracellular amino acid concentrations revealed significant accumulations of aspartate, glycine and threonine (FIG. 4e). A small but significant accumulation of glutamate also was observed following BCAT1 knockdown; however, considering the high ratio of media volume to intracellular volume, total concentration of glutamate is not significantly affected by this small intracellular accumulation. In the BCAT2 knockout mice the inhibition of BCAA catabolism results in high concentrations of BCAAs and higher rates of protein synthesis in peripheral tissues via the mechanistic target of rapamycin (mTOR) signaling pathway and compensatory increased protein degradation (increased protein turnover).

BCAT1 knockdown led to strong downregulation of 3-hydroxyacyl CoA dehydrogenase (HADH), an enzyme participating in the catabolism of valine and isoleucine downstream of BCAT1 (FIG. 4*f*, *g*). Since HADH is central to fatty acid metabolism, BCAT1 knockdown would also alter synthesis or degradation of fatty acids essential for membrane synthesis.

EXAMPLE 8

Limitation of Glioblastoma Migration in Microchannels by BCAT1 Knockdown

BCAT1 knockdown strongly affected cell morphology, resulting in a rounded, less extended appearance (FIG. 5*a-b*). To test whether these morphology changes could affect the tumor cells' ability to invade adjacent tissues, a microchannel migration chip to simulate a three-dimensional environment was used (FIG. 5*c*). Following BCAT1 knockdown, the majority of U-87MG cells (55%) penetrated short distances into the microchannels, but were unable to actively deform themselves in order to completely invade the microchannels whereas most control cells (78%) completely invaded the channels (FIG. 5*d*). This reduced invasiveness of the BCAT1 knockdown cells might be due to altered membrane composition caused by the observed lower abundance of long-chain fatty acids and differences in cholesterol metabolism (FIG. 4*g*); such changes might sufficiently affect general availability of membrane components as well as membrane elasticity to hinder cell invasion.

EXAMPLE 9

BCAT1 is Essential for Glioblastoma Growth

To assess the impact of BCAT1 on tumor cell proliferation, inhibition and knockdown experiments were conducted. A concentration-dependent reduction of proliferation up to 56%, estimated based on EdU-incorporation, was observed, upon treatment with the inhibitor gabapentin (FIG. 6*a*). Cell cycle analyses suggested that gabapentin treatment induced partial G1-arrest, indicated by the increased fraction of cells in G1-phase with concurrent decreases of the G2 and S-fractions (FIG. 6*b*). ShRNA-mediated BCAT1 knockdown elicited similar effects (FIG. 6*c*,d). BCAT1 knockdown decreased proliferation by 20-70% in all three cell lines (FIG. 6*c*) and led to G1-arrest and strong increases in cellular CDKN1B/p27$^{KIP1}$. Notably, the degree of CDKN1B/p27$^{KIP1}$ accumulation showed a positive correlation with the size of the G1-fraction (FIG. 6*d*). Cell death, indicated by the fraction of cells in sub-G1 phase, remained below 5% except in the case of Hs683, which showed a moderate increase as shown in the following Table 4

| Cell line | Treatment | Average sub-G1 [%] | STDEV sub-G1 |
|---|---|---|---|
| U87-MG | nt shRNA | 2.1 | 0.241 |
|  | BCAT1 shRNAI | 1.4 | 0.100 |
|  | BCAT1 shRNAII | 1.9 | 0.058 |
|  | 20 mM Gabapentin | 2.4 | 0.354 |
|  | Control (HEPES) | 1.4 | 0.707 |
| U373-MG | nt shRNA | 2.4 | 0.283 |
|  | BCAT1 ShRNAI | 1.1 | 0.045 |
|  | BCAT1 shRNAII | 2.7 | 0.141 |
|  | 20 mM Gabapentin | 2.8 | 0.283 |
|  | Control (HEPES) | 1.4 | 0.212 |
| HS683 | nt shRNA | 13.3 | 1.344 |
|  | BCAT1 shRNAI | 21.4 | 0.424 |
|  | BCAT1 shRNAII | 16.7 | 2.263 |
|  | 20 mM Gabapentin | 10.1 | 0.849 |
|  | Control (HEPES) | 2.2 | 0.424 |

Comparable reductions of cell proliferation were observed upon BCAT1 knockdown in glioblastoma primary spheroid cultures in serum-free media, except that these cells showed a higher rate of apoptosis as determined by Annexin V/7AAD staining (FIG. 9). Consistent with the observed reduction in proliferation, BCAT1 knockdown led to decreased phosphorylation of the v-akt murine thymoma viral oncogene homolog (AKT) in U-87MG, U-373MG and Hs683 cells (FIG. 6*e*).

The effect of BCAT1 knockdown on tumor growth in vivo was evaluated by intracerebral transplantation of U-87MG cells into CD-1 nude mice (FIG. 6*f-h*). Four weeks after transplantation of equal numbers of living cells, all 6 control mice, but only 1 of 6 mice transplanted with BCAT1-shRNA-transduced cells displayed neurologic symptoms such as lethargy or uncoordinated motor activities. Hematoxylin and eosin staining of mouse brain sections revealed large tumors in mice transplanted with control cells (FIG. 6*f*) while significantly smaller tumors were found in mice transplanted with BCAT1-knockdown cells (FIG. 6*g*). Quantitative analysis confirmed significant differences in tumor volume between the groups (FIG. 6*h*, P=0.0091).

The invention claimed is:

1. A method of treating a brain tumor comprising administering to a subject in need thereof a compound capable of reducing or inhibiting (a) the biological activity of branched-chain-aminotransferase-1 (BCAT1) or (b) the expression of the gene encoding BCAT1, thereby reducing or inhibiting the proliferation of brain tumor cells in the subject.

2. The method of claim 1, wherein said compound is an antisense oligonucleotide or siRNA reducing or inhibiting the expression of the gene encoding BCAT1.

3. The method of claim 1, wherein said compound is a compound reducing or inhibiting the biological activity of BCAT1.

4. The method of claim 3, wherein said compound is 1-(aminomethyl) cyclohexaneacetic acid.

5. The method of claim 3, wherein said compound is an antibody directed against BCAT1 or a fragment thereof.

6. The method of claim 1, wherein said compound is an inactive version of BCAT1.

7. The method of claim 1, wherein the neoplasm to be treated shows BCAT1 (over) expression.

8. The method of claim 1, wherein said brain tumor to be treated is an astrocytic brain tumor, glioma or glioblastoma.

9. The method of claim 8, wherein the brain tumor is an $IDH^{wt}$ glioblastoma.

* * * * *